(12) United States Patent
Breu et al.

(10) Patent No.: US 6,900,226 B2
(45) Date of Patent: May 31, 2005

(54) NEUROPEPTIDE Y ANTAGONISTS

(75) Inventors: Volker Breu, Schliengen (DE); Frank Dautzenberg, Muellheim (DE); Philippe Guerry, Binningen (CH); Matthias Heinrich Nettekoven, Grenzach-Wyhlen (DE); Philippe Pflieger, Schwoben (FR)

(73) Assignee: Hoffman-La Roche Inc., Nutley, NJ (US)

( * ) Notice: Subject to any disclaimer, the term of this patent is extended or adjusted under 35 U.S.C. 154(b) by 155 days.

(21) Appl. No.: 09/939,883

(22) Filed: Aug. 27, 2001

(65) Prior Publication Data

US 2002/0052356 A1 May 2, 2002

(30) Foreign Application Priority Data

Sep. 6, 2000  (EP) ............................................ 00119262

(51) Int. Cl.[7] ...................... A61K 31/55; A61K 31/517; C07D 403/00; C07D 419/00; C07D 215/38
(52) U.S. Cl. ............. 514/313; 514/210.21; 514/217.06; 514/266.2; 514/266.22; 540/599; 540/600; 544/284; 546/144; 546/159
(58) Field of Search ................... 514/210.21, 217.06, 514/266.2, 266.22, 313; 540/599, 600; 544/284; 546/159, 144

(56) References Cited

U.S. PATENT DOCUMENTS

| | | | |
|---|---|---|---|
| 4,598,089 A | | 7/1986 | Hadvary et al. ............. 514/449 |
| 6,004,996 A | | 12/1999 | Shah et al. .................. 514/449 |
| 6,576,644 B2 | * | 6/2003 | Bi et al. ....................... 514/313 |
| 6,696,467 B2 | * | 2/2004 | Mattei et al. ................ 514/313 |
| 6,787,558 B2 | * | 9/2004 | Klug et al. .................. 514/313 |
| 6,818,767 B2 | * | 11/2004 | Mueller et al. ............. 544/128 |
| 2003/0153553 A1 | * | 8/2003 | Mattei et al. .......... 514/217.07 |
| 2003/0158179 A1 | * | 8/2003 | Klug et al. ............ 514/217.07 |
| 2004/0029901 A1 | * | 2/2004 | Mattei et al. ............ 514/266.2 |
| 2004/0072818 A1 | * | 4/2004 | Dunning et al. ....... 514/210.21 |
| 2004/0077644 A1 | * | 4/2004 | Chapdelaine et al. .... 514/232.8 |

FOREIGN PATENT DOCUMENTS

| | | |
|---|---|---|
| EP | 185 359 | 6/1986 |
| EP | 189 577 | 8/1986 |
| EP | 443 449 | 8/1991 |
| EP | 524 495 | 1/1993 |
| WO | WO 86 06721 | 11/1986 |
| WO | WO 97 09308 | 2/1997 |
| WO | WO 99/34786 | 7/1999 |
| WO | WO 00/09123 | 2/2000 |
| WO | WO 01 02385 | 1/2001 |
| WO | 02/02549 * | 1/2002 |

OTHER PUBLICATIONS

Thompson et al., J. Org.Chem. 49, pp. 5237–5243 (1984).
Ishiyama et al., J. Org. Chem. 60, pp. 7508–7510 (1995).
Miyaura et al., Chem. Rev. 95, pp. 2457–2483 (1995).
J. K. Stille, Angew. Chem. 98, 508–524 (1986).
S. P. Stanfor, Tetrahedron 54, pp. 263–303 (1998).
Widdowson et al., Tetrahedron 42, pp. 2111–2116(1986).
E. I. Negishi, Acc. Chem. Res. 15, pp. 340–348 (1982).
Webber et al., J. Med. Chem. 36, pp. 733–746 (1993).
Chem. Abstracts, XP002190201 for Heterocycl. Commun., Korodi, Ferenc, 1(1), pp. 59–68 (1994).
Chem. Abstracts, XP002190202 for Farmaco, Savini, Luisa, et al., 49(10), pp. 633–699 (1994).
Chem. Abstracts, XP 002190203 for Arch., Pharm., Sathi Garima, et al., 316(9), pp. 767–772 (1983).
Chem. Abstracts, XP002190204 for Khim.–Farm. Zh., Yakhontov., L.N., et al., 9(11), pp. 12–18 (1975).

* cited by examiner

Primary Examiner—James O. Wilson
Assistant Examiner—Tamthom N. Trunong
(74) Attorney, Agent, or Firm—George W. Johnston; Dennis P. Tramaloni; Samuel H. Megerditchain

(57) ABSTRACT

Quinoline and quinazoline derivatives can be used in the form of pharmaceutical preparations as Neuropeptide Y antagonists for the treatment or prevention of arthritis, cardiovascular diseases, diabetes, renal failure, eating disorders and obesity.

76 Claims, No Drawings

NEUROPEPTIDE Y ANTAGONISTS

FIELD OF THE INVENTION

The present invention is concerned with novel quinoline and quinazoline derivatives useful as neuropeptide Y (NPY) receptor ligands, particularly neuropeptide Y (NPY) antagonists.

BACKGROUND OF THE INVENTION

Neuropetide Y is a 36 amino acid peptide that is widely distributed in the central and peripheral nervous systems. This peptide mediates a number of physiological effects through its various receptor subtypes. Studies in animals have shown that neuropeptide Y is a powerful stimulus of food intake, and it has been demonstrated that activation of neuropeptide Y Y5 receptors results in hyperphagia and decreased thermogenesis. Therefore compounds that antagonise neuropetide Y at the Y5 receptor subtype represent an approach to the treatment of eating disorders such as obesity and hyperphagia.

The current approach is aiming at medical intervention to induce weight loss or prevention of weight gain. This is achieved by interfering with appetite control, which is mediated by the Hypothalamus, an important brain region proven to control food intake. Herein, neuropeptide Y (NPY) has been proven to be one of the strongest central mediators of food intake in several animal species. Increased NPY levels result in profound food intake. Various receptors of neuropeptide Y (NPY) have been described to play a role in appetite control and weight gain. Interference with these receptors is likely to reduce appetite and consequently weight gain. Reduction and long-term maintenance of body weight can also have beneficial consequences on con associated risk factors such as arthritis, cardiovascular diseases, diabetes and renal failure.

SUMMARY OF THE INVENTION

The invention is concerned especially with compounds of formula I

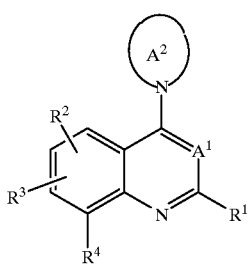

I wherein
$R^1$ is alkyl, cycloalkyl, aralkyl or trifluoroalkyl;
$R^2$ is hydrogen, alkyl, alkoxy, hydroxy, halogen, trifluoroalkyl, difluoroalkoxy or trifluoroalkoxy;
$R^3$ is aryl or heteroaryl;
pharmaceutically acceptable salts of compounds of Formula I, and
pharmaceutically acceptable esters of compounds of Formula I.

The compounds of of the invention are novel and have valuable pharmacological properties. They are neuropeptide ligands, for example neuropeptide receptor antagonists and in particular, they are selective neuropeptides Y Y5 receptor antagonists.

Accordingly, the compounds of the invention can be used in the prophylaxis or treatment of arthritis, cardiovascular diseases, diabetes, renal failure and particularly eating disorders and obesity.

Objects of the present invention are the compounds of the invention, including those of formulas I and Ia and their aforementioned salts per se, and their use as therapeutically active substances, a process for the manufacture of the said compounds, intermediates, pharmaceutical compositions, medicaments containing the said compounds, their pharmaceutically acceptable salts and solvates, the use of the said compounds, solvates and salts for the prophylaxis and/or therapy of illnesses, especially in the treatment or prophylaxis of arthritis, cardiovascular diseases, diabetes, renal failure and particularly eating disorders such as hyperphagia and particularly obesity, and the use of the said compounds and salts for the production of medicaments for the treatment or prophylaxis of arthritis, cardiovascular diseases, diabetes, renal failure and particularly eating disorders and obesity.

DETAILED DESCRIPTION OF THE INVENTION

In the present description the term "alkyl", alone or in combination, signifies a straight-chain or branched-chain alkyl group with 1 to 8 carbon atoms, preferably a straight or branched-chain alkyl group with 1 to 6 carbon atoms and particularly preferred a straight or branched-chain alkyl group with 1 to 4 carbon atoms Examples of straight-chain and branched $C_1$–$C_8$ alkyl groups are methyl, ethyl, propyl, isopropyl, butyl, isobutyl, tert.-butyl, the isomeric pentyls, the isomeric hexyls, the isomeric heptyls and the isomeric octyls, preferably methyl and ethyl and most preferred methyl.

The term "cycloalkyl", alone or in combination, signifies a cycloalkyl ring with 3 to 8 carbon atoms and preferably a cycloalkyl ring with 3 to 6 carbon atoms. Examples of $C_3$–$C_8$ cycloalkyl are cyclopropyl, methyl-cyclopropyl, dimethylcyclopropyl, cyclobutyl, methyl-cyclobutyl, cyclopentyl, methyl-cyclopentyl, cyclohexyl, methyl-cyclohexyl, dimethyl-cyclohexyl, cycloheptyl and cyclooctyl, preferably cyclopropyl and particularly cyclopentyl.

The term "alkoxy", alone or in combination, signifies a group of the formula alkyl-O— in which the term "alkyl" has the previously given significance, such as methoxy, ethoxy, n-propoxy, isopropoxy, n-butoxy, isobutoxy, sec. butoxy and tert.butoxy, 2-hydroxyethoxy, 2-methoxyethoxypreferably methoxy and ethoxy and most preferred methoxy.

The term "alkoxyalkoxy", alone or in combination, signifies a group of the formula alkyl-O-alkyl-O— in which the term "alkyl" has the previously given significance. A preferred example is 2-methoxyethoxy.

The term "hydroxyalkoxy", alone or in combination, signifies alkoxy group as previously described in which one hydrogen atom has been replaced by a hydroxy group. Examples are hydroxymethoxy and preferably 2-hydroxyethoxy.

The term "aryl", alone or in combination, signifies a phenyl or naphthyl group which optionally carries one or more, particularly one to three substituents each independently selected from halogen, trifluoromethyl, amino, alkyl, alkoxy, aryloxy, alkylcarbonyl, cyano, carbamoyl, alkoxycarbamoyl, methylendioxy, carboxy, alkoxycarbonyl, aminocarbonyl, alkyaminocarbonyl, dialkylaminocarbonyl, hydroxy, nitro and the like, such as phenyl, chlorophenyl, trifluoromethylphenyl, chlorofluorophenyl, aminophenyl, methylcarbonylphenyl, methoxyphenyl, methylendioxyphenyl, 1-naphthyl and 2-naphthyl. Preferred is phenyl. Preferred substituents of phenyl and naphthyl are halogen, trifluoromethyl, amino, alkoxy, methylendioxy, alkylcarbonyl, cyano, alkyl, nitro, hydroxy, trifluoromethoxy, alkylsulfanyl, alkenyl, alkoxycarbonyl, aryloxy, alkoxycarbonylamino, alkylcarbonylamino and aminocarbonyl.

The term "aralkyl", alone or in combination, signifies an alkyl or cycloalkyl group as previously defined in which one hydrogen atom has been replaced by an aryl group as previously defined. Preferred are benzyl, benzyl substituted with hydroxy, alkoxy or halogen, preferably fluorine. Particularly preferred is benzyl.

The term "heterocyclyl", alone or in combination, signifies a saturated, partially unsaturated or aromatic 4- to 10-membered heterocycle which contains one or more, preferably one ore two hetero atoms selected from nitrogen, oxygen and sulfur, wherein oxygen and particularly nitrogen are preferred. If desired, it can be substituted on one or more carbon atoms by halogen, alkyl, alkoxy, oxo etc. and/or on a secondary nitrogen atom (i.e. —NH—) by alkyl, cycloalkyl, aralkoxycarbonyl, alkanoyl, phenyl or phenylalkyl or on a tertiary nitrogen atom (i.e. =N—) by oxido, with halogen, alkyl, cycloalkyl and alkoxy being preferred. Examples of such heterocyclyl groups are pyrrolidinyl, piperidinyl, morpholinyl, piperazinyl, 3,4-dihydro-1H-isoquinolinyl or azepanyl, wherein each of these rings can be substituted with alkyl. Particularly preferred are pyrrolidinyl, piperidinyl, morpholinyl, 4-methylpiperazinyl, 3,4-dihydro-1H-isoquinolinyl or azepanyl.

The term "heteroaryl", alone or in combination, signifies aromatic 5- to 10-membered heterocycle which contains one or more, preferably one ore two hetero atoms selected from nitrogen, oxygen and sulfur, wherein nitrogen or oxygen are preferred. If desired, it can be substituted on one or more, preferably on one to three carbon atoms e.g. by halogen, trifluoromethyl, amino, alkoxy, methylendioxy, alkylcarbonyl, cyano, alkyl, nitro, hydroxy, trifluoromethoxy, alkylsulfanyl, alkenyl, alkoxycarbonyl, aryloxy, alkoxycarbonylamino, alkylcarbonylamino or aminocarbonyl. Examples of such heteroaryl groups are thiophenyl, pyridinyl, pyrazinyl and pyrimidinyl, benzofuryl, 1H-indolyl, benzothiophenyl, and benzothiofuranyl. Preferred are thiophenyl, pyridinyl, pyrimidinyl, 1H-indolyl.

The term "amino", alone or in combination, signifies a primary, secondary or tertiary amino group bonded via the nitrogen atom, with the secondary amino group carrying an alkyl or cycloalkyl substituent and the tertiary amino group carrying two similar or different alkyl or cycloalkyl substituents or the two nitrogen substituents together forming a ring, such as, for example, —NH$_2$, methylamino, ethylamino, dimethylamino, diethylamino, methylethylamino, pyrrolidin-1-yl or piperidino etc., preferably amino, dimethylamino and diethylamino and particularly primary amino.

The term "halogen" signifies fluorine, chlorine, bromine or iodine and preferably fluorine, chlorine or bromine and particularly fluorine or chlorine.

The term "carboxy", alone or in combination, signifies a —COOH group.

The term "cyano", alone or in combination, signifies a —CN group.

The term "nitro", alone or in combination, signifies a —NO$_2$ group.

The term "carboxyalkyl" alone or in combination, signifies an alkyl group as previously described in which one hydrogen atom has been replaced by a carboxy group. The carboxymethyl group is preferred and particularly carboxyethyl.

The term "trifluoroalkyl" alone or in combination, signifies an alkyl group as previously described in which three hydrogen atoms have been replaced by three fluorine atoms. A preferred example is trifluoromethyl.

The term "difluoroalkoxy" alone or in combination, signifies an alkoxy group as previously described in which two hydrogen atoms have been replaced by two fluorine atoms. Examples are —O—CHF$_2$ and —O—CH$_2$CHF$_2$.

The term "trifluoroalkoxy" alone or in combination, signifies an alkoxy group as previously described in which three hydrogen atoms have been replaced by tree fluorine atoms. Examples are —O—CF$_3$, —O—CH$_2$CF$_3$. Preferred is —O—CF$_3$.

Examples of pharmaceutically acceptable salts of the compounds of formula I are salts with physiologically compatible mineral acids such hydrochloric acid, sulfuric acid or phosphoric acid; or with organic acids such as methanesulfonic acid, acetic acid, trifluoroacetic acid, citric acid, fumaric acid, maleic acid, tartaric acid, succinic acid or salicylic acid. Preferred is formic acid. The compounds of formula I with free carboxy groups can also form salts with physiologically compatible bases. Examples of such salts are alkali metal, alkali earth metal, ammonium and alkylammonium salts such as the Na, K, Ca or tertramethylammonium salt. The compound of formula I can also be present in the form of zwitterions.

The compounds of formula I can also be solvated, e.g. hydrated. The solvation can be effected in the course of the manufacturing process or can take place e.g. as a consequence of hygroscopic properties of an initially anhydrous compound of formula I (hydration).

The term pharmaceutically acceptable esters of the compounds of formula I means that compounds of formula (I) may be derivatised at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compounds of formula (I), similar to the metabolically labile esters, which are capable of producing the parent compounds of formula (I) in vivo, are within the scope of this invention.

In more detail, for example, the COOH groups of compounds according to formula I can be esterified. The alkyl and aralkyl esters are examples of suitable esters. The methyl, ethyl, propyl, butyl and benzyl esters are preferred esters. The methyl and ethyl esters are especially preferred. Further examples of pharmaceutically acceptable esters are compounds of formula I, wherein the hydroxy groups can be esterified. Examples of such esters are formate, acetate, propionate, butyrate, isobutyrate, valerate, 2-methylbutyrate, isovalerate and N,N-dimethylaminoacetate. Preferred esters are acetate and N,N-dimethylaminoacetate.

The term "lipase inhibitor" refers to compounds which are capable of inhibiting the action of lipases, for example gastric and pancreatic lipases. For example orlistat and lipstatin as described in U.S. Pat. No. 4,598,089 are potent inhibitor of lipases. Lipstatin is a natural product of microbial origin, and orlistat is the result of a hydrogenation of lipstatin. Other lipase inhibitors include a class of compound commonly referred to as panclicins. Panclicins are analogues of orlistat (Mutoh et al, 1994). The term "lipase inhibitor" refers also to polymer bound lipase inhibitors for example described in International Patent Application WO99/34786 (Geltex Pharmaceuticals Inc.). These polymers are characterized in that they have been substituted with one or more groups that inhibit lipases. The term "lipase inhibitor" also comprises pharmaceutically acceptable salts of these compounds. The term "lipase inhibitor" preferably refers to orlistat.

Orlistat is a known compound useful for the control or prevention of obesity and hyperlipidemia. See, U.S. Pat. No. 4,598,089, issued Jul. 1, 1986, which also discloses processes for making orlistat and U.S. Pat. No. 6,004,996, which discloses appropriate pharmaceutical compositions. Further suitable pharmaceutical compositions are described for example in International Patent Applications WO 00/09122 and WO 00/09123. Additional processes for the preparation of orlistat are disclosed in European Patent Applications Publication Nos. 185,359, 189,577, 443,449, and 524,495.

Orlistat is preferably orally administered from 60 to 720 mg per day in divided doses two to three times per day. Preferred is wherein from 180 to 360 mg, most preferably 360 mg per day of a lipase inhibitor is administered to a subject, preferably in divided doses two or, particularly, three times per day. The subject is preferably an obese or overweight human, i.e. a human with a body mass index of 25 or greater. Generally, it is preferred that the lipase inhibitor be administered within about one or two hours of ingestion of a meal containing fat. Generally, for administering a lipase inhibitor as defined above it is preferred that treatment be administered to a human who has a strong family history of obesity and has obtained a body mass index of 25 or greater.

Orlistat can be administered to humans in conventional oral compositions, such as, tablets, coated tablets, hard and soft gelatin capsules, emulsions or suspensions. Examples of carriers which can be used for tablets, coated tablets, dragées and hard gelatin capsules are lactose, other sugars and sugar alcohols like sorbitol, mannitol, maltodextrin, or other fillers; surfactants like sodium lauryle sulfate, Brij 96, or Tween 80; disintegrants like sodium starch glycolate, maize starch or derivatives thereof; polymers like povidone, crospovidone; talc; stearic acid or its salts and the like. Suitable carriers for soft gelatin capsules are, for example, vegetable oils, waxes, fats, semi-solid and liquid polyols and the like. Moreover, the pharmaceutical preparations can contain preserving agents, solubilizers, stabilizing agents, wetting agents, emulsifying agents, sweetening agents, coloring agents, flavoring agents, salts for varying the osmotic pressure, buffers, coating agents and antioxidants. They can also contain still other therapeutically valuable substances. The formulations may conveniently be presented in unit dosage form and may be prepared by any methods known in the pharmaceutical art. Preferably, orlistat is administered according to the formulation shown in the Examples and in U.S. Pat. No. 6,004,996, respectively.

The compounds of formula I can contain several asymmetric centers and can be present in the form of optically pure enantiomers, mixtures of enantiomers such as, for example, racemates, optically pure diastereoisomers, mixtures of diastereoisomers, diastereoisomeric racemates or mixtures of diastereoisomeric racemates.

In the nomenclature used in the present application the ring atoms of the quinoline and the quinazoline rings are numbered as follows:

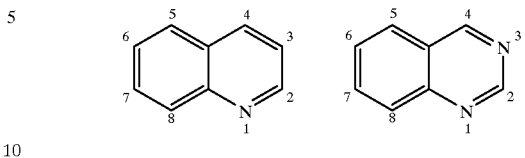

wherein, $R^4$ is attached at the 8-position. In a preferred embodiment of the present invention $R^3$ is attached at the 5- or 6-position. In a particularly preferred embodiment of the present invention $R^3$ is attached at the 7-position of the quinoline or quinazoline ring.

In another preferred embodiment of the invention $R^2$ is attached at the 7-position and particularly preferred at the 5- or 6-position.

Preferred are compounds according to formula I and pharmaceutically acceptable salts and solvates thereof.

Also preferred are compounds of formula I, wherein $R^2$ is hydrogen, alkyl, alkoxy, hydroxy, trifluoroalkyl, difluoroalkoxy or trifluoroalkoxy. Particularly preferred compounds of formula I are those, wherein $R^2$ is hydrogen, methyl, methoxy, ethoxy, fluoro, chloro, —O—$CHF_2$ or —O—$CF_3$. Most preferred is hydrogen.

Another preferred aspect of the present invention are compounds according to formula I, wherein $R^1$ is alkyl. Particularly preferred is ethyl and most preferred is methyl.

Likewise preferred are compounds of formula I, wherein $A^1$ is CH.

Other preferred compounds of formula I are those, wherein $A^1$ is N.

Further preferred are compounds according to formula I, wherein $R^3$ is unsubstituted phenyl, thiophenyl, pyridinyl, pyrimidinyl, 1H-indolyl, benzofuryl, benzothiophenyl or naphthyl or $R^3$ is phenyl, thiophenyl, pyridinyl, pyrimidinyl, 1H-indolyl, benzofuryl, benzothiophenyl or naphthyl, substituted with one to three substituents each independently selected from halogen, trifluoromethyl, amino, alkoxy, methylendioxy, alkylcarbonyl, cyano, alkyl, nitro, hydroxy, trifluoromethoxy, alkylsulfanyl, alkenyl, alkoxycarbonyl, aryloxy, alkoxycarbonylamino, alkylcarbonylamino and aminocarbonyl.

Further preferred are compounds according to formula I, wherein $R^3$ is unsubstituted thiophenyl, pyridinyl or naphthyl or $R^3$ is phenyl or thiophenyl substituted with one or two substituents each independently selected from halogen, trifluoromethyl, alkoxy, alkylcarbonyl, cyano and hydroxy.

Particularly preferred are compounds according to formula I, wherein $R^3$ is unsubstituted thiophenyl, pyridinyl or naphthyl or $R^3$ is phenyl or thiophenyl substituted with one or two substituents each independently selected from fluoro, chloro, trifluoromethyl, methoxy, methylcarbonyl, cyano and hydroxy.

Also preferred are compounds according to formula I, wherein $R^3$ is phenyl or phenyl substituted with one to three substituents, preferably one, each independently selected from halogen, trifluoromethyl, amino, alkoxy, methylendioxy, alkylcarbonyl and cyano or $R^3$ is thiophenyl, pyridinyl, pyrimidinyl, 1H-indolyl or benzofuryl. Particularly preferred are these compounds, wherein $R^3$ is phenyl or phenyl substituted with fluoro, chloro, trifluoromethyl, primary amino, methoxy, ethoxy, methylcarbonyl and/or ethylcarbonyl or $R^3$ is thiophenyl, pyridinyl, pyrimidinyl or 1H-indolyl. Most preferred are these compounds, wherein $R^3$ is phenyl or phenyl substituted with chloro, trifluoromethyl, primary amino, methoxy, ethoxy and/or methylcarbonyl or R³ is thiophenyl, pyridinyl, pyrimidinyl or 1H-indolyl.

Also preferred compounds according to formula I are those, wherein A² is a 4- to 10-membered heterocyclic ring optionally substituted with alkyl. Particularly preferred are those compounds, wherein A² is a 5- to 7-membered monocyclic or a 10-membered bicyclic heterocyclic ring optionally substituted with alkyl.

Further preferred are these compounds, wherein A² is a pyrrolidine, piperidine, morpholine, piperazine, 3,4-dihydro-1H-isoquinoline or azepane ring, wherein these rings are optionally substituted with alkyl. Most preferred are these compounds, wherein A² is a pyrrolidine, piperidine, morpholine, 4-methyl-piperazine, 3,4-dihydro-1H-isoquinoline or azepane ring.

Also preferred are compounds according to formula I, wherein R⁵ is hydrogen, methyl, ethyl or benzyl.

Further preferred are compounds of formula I, wherein R⁶ and R⁷ are hydrogen, methyl or ethyl.

Another preferred embodiment of the instant invention comprises compounds of Formula Ia

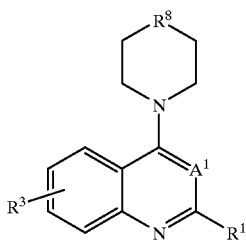

Ia wherein
R¹ is lower alkyl;
R³ is aryl or heteroaryl attached at the 5, 6 or 7-position of the quinoline or quinazoline ring;
A¹ is CH or N;
R⁸ is a bond, lower alkyl, O, N or N-alkyl;
pharmaceutically acceptable salts of compounds of Formula Ia, and
pharmaceutically acceptable esters of compounds of Formula Ia.

Examples of preferred compounds of Formula I and Formula Ia are:
7-(3-Chloro-phenyl)-2-methyl-4-pyrrolidin-1-yl-quinoline;
2-methyl-4-pyrrolidin-1-yl-7-(3-trifluoromethyl-phenyl)-quinoline;
3-(2-methyl-4-pyrrolidin-1-yl-quinolin-7-yl)-phenylamine;
1-[4-(2-methyl-4-pyrrolidin-1-yl-quinolin-7-yl)-phenyl]-ethanone;
2-methyl-7-phenyl-4-pyrrolidin-1-yl-quinoline;
7-(4-methoxy-phenyl)-2-methyl-4-pyrrolidin-1-yl-quinoline;
2-methyl-4-pyrrolidin-1-yl-7-thiophen-2-yl-quinoline;
2-methyl-7-pyridin-3-yl-4-pyrrolidin-1-yl-quinoline;
2-methyl-7-pyrimidin-5-yl-4-pyrrolidin-1-yl-quinoline;
2-methyl-4-piperidin-1-yl-7-(3-trifluoromethyl-phenyl)-quinoline;
7-(3-chloro-phenyl)-2-methyl-4-piperidin-1-yl-quinoline;
1-[4-(2-methyl-4-piperidin-1-yl-quinolin-7-yl)-phenyl]-ethanone;
3-(2-methyl-4-piperidin-1-yl-quinolin-7-yl)-phenylamine;
7-(4-methoxy-phenyl)-2-methyl-4-piperidin-1-yl-quinoline;
2-methyl-4-piperidin-1-yl-7-thiophen-2-yl-quinoline;
2-methyl-7-phenyl-4-piperidin-1-yl-quinoline;
7-(1H-indol-5-yl)-2-methyl-4-piperidin-1-yl-quinoline;
2-methyl-4-piperidin-1-yl-7-pyridin-3-yl-quinoline;
2-methyl-4-morpholin-4-yl-7-(3-trifluoromethyl-phenyl)-quinoline;
1-[4-(2-methyl-4-morpholin-4-yl-quinolin-7-yl)-phenyl]-ethanone;
2-methyl-4-(4-methyl-piperazin-1-yl)-7-(3-trifluoromethyl-phenyl)-quinoline;
4-(3,4-dihydro-1H-isoquinolin-2-yl)-2-methyl-7-(3-trifluoromethyl-phenyl)-quinoline;
5-(3-chloro-phenyl)-2-methyl-4-piperidin-1-yl-quinoline;
2-methyl-4-piperidin-1-yl-5-(3-trifluoromethyl-phenyl)-quinoline;
5-(3-chloro-phenyl)-2-methyl-4-pyrrolidin-1-yl-quinoline;
5-(3-chloro-phenyl)-2-methyl-4-morpholin-4-yl-quinoline;
4-azepan-1-yl-2-methyl-7-(3-trifluoromethyl-phenyl)-quinoline;
6-(3-chloro-phenyl)-2-methyl-4-pyrrolidin-1-yl-quinoline;
7-(3-chloro-phenyl)-4-pyrrolidin-1-yl-quinoline;
2-methyl-4-piperidin-1-yl-7-(3-trifluoromethyl-phenyl)-quinazoline;
7-(4-methoxy-phenyl)-2-methyl-4-piperidin-1-yl-quinazoline;
3-(2-methyl-4-piperidin-1-yl-quinazolin-7-yl)-phenylamine;
2-methyl-4-piperidin-1-yl-7-pyridin-3-yl-quinazoline;
2-methyl-7-pyrimidin-5-yl-4-pyrrolidin-1-yl-quinazoline;
2-methyl-4-pyrrolidin-1-yl-7-(3-trifluoromethyl-phenyl)-quinazoline;
7-(3-chloro-phenyl)-2-methyl-4-pyrrolidin-1-yl-quinazoline;
7-(3-chloro-phenyl)-2-methyl-4-piperidin-1-yl-quinazoline;
4-azepan-1-yl-2-methyl-7-(3-trifluoromethyl-phenyl)-quinazoline;
7-(4-methoxy-phenyl)-2-methyl-4-pyrrolidin-1-yl-quinazoline;
2-methyl-4-pyrrolidin-1-yl-7-thiophen-3-yl-quinazoline;
[4-(2-methyl-4-pyrrolidin-1-yl-quinazolin-7-yl)-phenyl]-carbamic acid tert-butyl ester;
3-(2-methyl-4-pyrrolidin-1-yl-quinazolin-7-yl)-benzonitrile;
7-(3,5-dichloro-phenyl)-2-methyl-4-pyrrolidin-1-yl-quinazoline;
1-[3-(2-methyl-4-pyrrolidin-1-yl-quinazolin-7-yl)-phenyl]-ethanone;
2-methyl-4-pyrrolidin-1-yl-7-(4-trifluoromethyl-phenyl)-quinazoline;
2-methyl-4-pyrrolidin-1-yl-7-thiophen-2-yl-quinazoline;
1-[5-(2-methyl-4-pyrrolidin-1-yl-quinazolin-7-yl)-thiophen-2-yl]-ethanone;
7-(1H-indol-5-yl)-2-methyl-4-pyrrolidin-1-yl-quinazoline;
N-[2-methyl-4-(2-methyl-4-pyrrolidin-1-yl-quinazolin-7-yl)-phenyl]-acetamide;
2-methyl-7-(3-nitro-phenyl)-4-pyrrolidin-1-yl-quinazoline;
3-(2-methyl-4-pyrrolidin-1-yl-quinazolin-7-yl)-phenylamine;
3-(2-methyl-4-pyrrolidin-1-yl-quinazolin-7-yl)-phenol;
2-methyl-4-pyrrolidin-1-yl-7-(3-trifluoromethoxy-phenyl)-quinazoline;
2-methyl-7-phenyl-4-pyrrolidin-1-yl-quinoline;
7-(4-ethyl-phenyl)-2-methyl-4-pyrrolidin-1-yl-quinoline;
7-(3,4-dimethoxy-phenyl)-2-methyl-4-pyrrolidin-1-yl-quinoline;
7-(2,6-difluoro-phenyl)-2-methyl-4-pyrrolidin-1-yl-quinoline;
7-(2,4-dimethoxy-phenyl)-2-methyl-4-pyrrolidin-1-yl-quinoline;

2-methyl-4-pyrrolidin-1-yl-7-(4-trifluoromethyl-phenyl)-quinoline;
2-methyl-7-(4-methylsulfanyl-phenyl)-4-pyrrolidin-1-yl-quinoline;
7-(2-methoxy-phenyl)-2-methyl-4-pyrrolidin-1-yl-quinoline;
7-(3-ethoxy-phenyl)-2-methyl-4-pyrrolidin-1-yl-quinoline;
N-[3-(2-methyl-4-pyrrolidin-1-yl-quinolin-7-yl)-phenyl]-acetamide;
2-methyl-4-pyrrolidin-1-yl-7-(4-trifluoromethoxy-phenyl)-quinoline;
7-benzo[1,3]dioxol-5-yl-2-methyl-4-pyrrolidin-1-yl-quinoline;
7-benzofuran-2-yl-2-methyl-4-pyrrolidin-1-yl-quinoline;
7-benzo[b]thiophen-2-yl-2-methyl-4-pyrrolidin-1-yl-quinoline;
7-(3-chloro-4-fluoro-phenyl)-2-methyl-4-pyrrolidin-1-yl-quinoline;
1-[5-(2-methyl-4-pyrrolidin-1-yl-quinolin-7-yl)-thiophen-2-yl]-ethanone;
7-(3,4-dichloro-phenyl)-2-methyl-4-pyrrolidin-1-yl-quinoline;
7-(2-fluoro-phenyl)-2-methyl-4-pyrrolidin-1-yl-quinoline;
2-methyl-7-naphthalen-1-yl-4-pyrrolidin-1-yl-quinoline;
7-(2-chloro-phenyl)-2-methyl-4-pyrrolidin-1-yl-quinoline;
2-methyl-4-pyrrolidin-1-yl-7-(4-vinyl-phenyl)-quinoline;
7-(3,5-bis-trifluoromethyl-phenyl)-2-methyl-4-pyrrolidin-1-yl-quinoline;
7-(3-methoxy-phenyl)-2-methyl-4-pyrrolidin-1-yl-quinoline;
3-(2-methyl-4-pyrrolidin-1-yl-quinolin-7-yl)-benzoic acid ethyl ester;
4-(2-methyl-4-pyrrolidin-1-yl-quinolin-7-yl)-benzoic acid ethyl ester;
2-methoxy-4-(2-methyl-4-pyrrolidin-1-yl-quinolin-7-yl)-phenol;
N-[4-(2-methyl-4-pyrrolidin-1-yl-quinolin-7-yl)-phenyl]-acetamide;
dimethyl-[4-(2-methyl-4-pyrrolidin-1-yl-quinolin-7-yl)-phenyl]-amine;
7-(3,5-dichloro-phenyl)-2-methyl-4-pyrrolidin-1-yl-quinoline;
2-methyl-7-naphthalen-2-yl-4-pyrrolidin-1-yl-quinoline;
N-methyl-4-(2-methyl-4-pyrrolidin-1-yl-quinolin-7-yl)-benzamide;
3-(2-methyl-4-pyrrolidin-1-yl-quinolin-7-yl)-phenol;
2-methoxy-5-(2-methyl-4-pyrrolidin-1-yl-quinolin-7-yl)-phenol;
7-(2,6-dimethoxy-pyridin-3-yl)-2-methyl-4-pyrrolidin-1-yl-quinoline;
2-(2-methyl-4-pyrrolidin-1-yl-quinolin-7-yl)-phenol;
2-methyl-7-(4-phenoxy-phenyl)-4-pyrrolidin-1-yl-quinoline;
7-(2,6-dichloro-phenyl)-2-methyl-4-pyrrolidin-1-yl-quinoline;
2-methyl-4-pyrrolidin-1-yl-7-(3-trifluoromethoxy-phenyl)-quinoline and
2-methyl-4-pyrrolidin-1-yl-7-(2-trifluoromethoxy-phenyl)-quinoline.

Examples of particularly preferred compounds of Formulas I and Ia are:
7-(3-Chloro-phenyl)-2-methyl-4-pyrrolidin-1-yl-quinoline;
2-methyl-4-pyrrolidin-1-yl-7-(3-trifluoromethyl-phenyl)-quinoline;
1-[4-(2-methyl-4-pyrrolidin-1-yl-quinolin-7-yl)-phenyl]-ethanone;
7-(4-methoxy-phenyl)-2-methyl-4-pyrrolidin-1-yl-quinoline;
2-methyl-4-pyrrolidin-1-yl-7-thiophen-2-yl-quinoline;
2-methyl-7-pyridin-3-yl-4-pyrrolidin-1-yl-quinoline;
2-methyl-4-piperidin-1-yl-7-(3-trifluoromethyl-phenyl)-quinoline;
5-(3-chloro-phenyl)-2-methyl-4-piperidin-1-yl-quinoline;
4-azepan-1-yl-2-methyl-7-(3-trifluoromethyl-phenyl)-quinoline;
2-methyl-4-pyrrolidin-1-yl-7-(3-trifluoromethyl-phenyl)-quinazoline;
7-(3-chloro-phenyl)-2-methyl-4-pyrrolidin-1-yl-quinazoline;
4-azepan-1-yl-2-methyl-7-(3-trifluoromethyl-phenyl)-quinazoline;
3-(2-methyl-4-pyrrolidin-1-yl-quinazolin-7-yl)-benzonitrile;
1-[3-(2-methyl-4-pyrrolidin-1-yl-quinazolin-7-yl)-phenyl]-ethanone;
7-(3-chloro-4-fluoro-phenyl)-2-methyl-4-pyrrolidin-1-yl-quinoline;
1-[5-(2-methyl-4-pyrrolidin-1-yl-quinolin-7-yl)-thiophen-2-yl]-ethanone;
7-(3,4-dichloro-phenyl)-2-methyl-4-pyrrolidin-1-yl-quinoline;
2-methoxy-4-(2-methyl-4-pyrrolidin-1-yl-quinolin-7-yl)-phenol;
7-(3,5-dichloro-phenyl)-2-methyl-4-pyrrolidin-1-yl-quinoline and
2-methyl-7-naphthalen-2-yl-4-pyrrolidin-1-yl-quinoline.

Further preferred compounds of the present invention are:
diethyl-[2-methyl-7-(3-trifluoromethyl-phenyl)-quinolin-4-yl]-amine;
[7-(3-amino-phenyl)-2-methyl-quinolin-4-yl]-diethyl-amine;
1-[4-(4-diethylamino-2-methyl-quinolin-7-yl)-phenyl]-ethanone;
and pharmaceutically acceptable salts, solvates and esters thereof.

Processes for the manufacture of compounds of formula I are an object of the invention.

The substituents and indices used in the following description of the processes have the significance given above unless indicated to the contrary.

Compounds of formula I

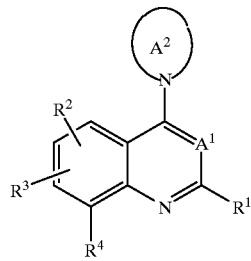

I wherein $R^1$ to $R^4$, $A^1$ and $A^2$ are defined as before can be prepared as follows:

According to scheme A compounds of formula I can be obtained by the reaction of a compound of the formula IIIa with a compound of formula IIa. Alternatively, compounds of formula I can be prepared as shown in scheme B. wherein a compound of formula IIIb is reacted in the presence of a compound of the formula IIb.

Scheme A

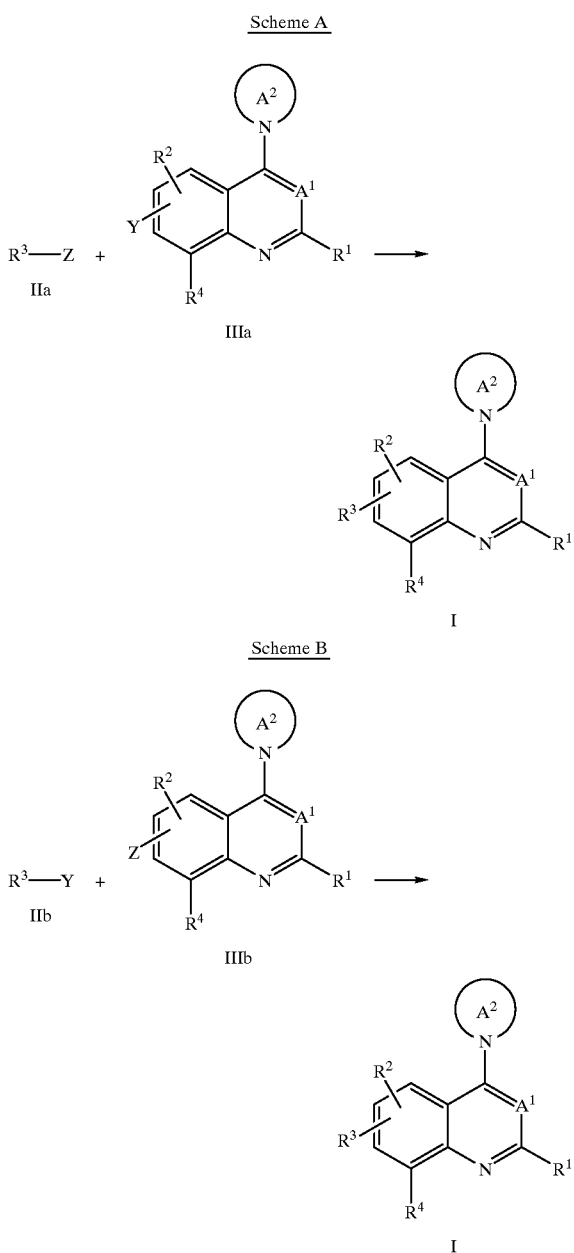

Scheme B

In both schemes, A and B, $R^1$, $R^2$, $R^3$, $R^4$, $A^1$ and $A^2$ are defined as before and Y and Z are substituents or groups which can be used in transition metal catalyzed cross coupling reactions. For example Y can be iodine, bromine, chlorine, methylsulfonyloxy, trifluoromethylsulfonyloxy, phenylsulfonyloxy or p-tosylsulfonyloxy and Z is for example $(OH)_2B—$ or $(R'O)_2B—$, wherein R' is methyl) ethyl, isopropyl or the two R' form together a cyclic diester such as 1,3-propyldioxy- or 2,3-dimethyl-2,3-butanedioxy-). (W. Thompson, J. Gaudino, J. Org. Chem. 1984, 49, 5237–5243; T. Ishiyama, M. Murata, N. Miyaura, J. Org. Chem. 1995, 60, 7508–7510). This reaction, also known as a "Suzuki coupling" (N. Miyaura and A. Suzuki, Chem. Rev. 1995, 95, 2457–2483), is preferably effected in an inert organic solvent such as e.g. dimethoxyethane, dioxan, dimethylformamide or tetrahydrofuran at a temperature between about 20° C. and the boiling point of the reaction mixture. A further solvent or cosolvent is preferably added to the reaction mixture. Preferably, a base such an alkali metal carbonate, e.g. sodium carbonate, barium hydroxide, potassium phosphate or potassium fluoride is preferably added as a solid or as an aqueous solution to the reaction mixture. Preferably, the reaction is performed in the presence of a transition metal complex such as a nickel or palladium metal complex, preferably a palladium complex such as tetrakis-triphenylphosphine-palladium or dichloro [1,1'-Bis(diphenylphosphino)-ferrocene]-palladium (II) dichloromethan.

Alternatively, substituent Z in scheme A or B can be $Sn(alkyl)_3$, e.g. $—Sn(CH_3)_3$ or $—Sn(n-butyl)_3$ ("Stille reaction", J. K. Stille, Angew. Chem. 1986, 98, 504–519; S. P. Stanford, Tetrahedron, 1998, 54, 263–303); or MgHal or Li("Kharasch" reaction, D. A. Widdowson, Y.-Z. Zhang, Tetrahedron, 1986, 42, 211–2116); or ZnHal, wherein Hal is bromine, iodine or chlorine; ("Negishi" reaction, E. I. Negishi, Acc. Chem. Res. 1982, 15, 340–348).

The reactions can be effected in the absence of a base in an inert solvent such as e.g. dimethoxyethane, dioxan or tetrahydrofuran at a temperature between about –20° C. and the boiling point of the reaction mixture. It can also be advantageous to add an inert salt, especially lithium chloride. A transition metal complex such as a nickel or palladium metal complex, preferably a palladium metal complex can be present in the reaction mixture. A preferred palladium metal complex is tetrakis-triphenylphosphine-palladium.

The manufacture of the starting materials of formulas IIIa and IIIb can be effected in a manner known per se, e.g. by reacting a 4 chloroquinoline of type IV or a 4 chloroquinazoline of type IV with the corresponding amine of formula V

V conveniently in a polar solvent in the presence of a proton binding reagent at a temperature between 20° C. and the boiling point of the reaction mixture. It can be advantageous to add catalytic amounts of an iodide salt, preferably potassium iodide to the reaction mixture. Preferably used solvents are lower alkanol such as methanol or ethanol, isopropanol or n-butanol. Preferably, proton binding reagents are in excess of the amine used in the reaction or an organic base such as triethylamin or pyridine or an inorganic base such as alkalimetal carbonates.

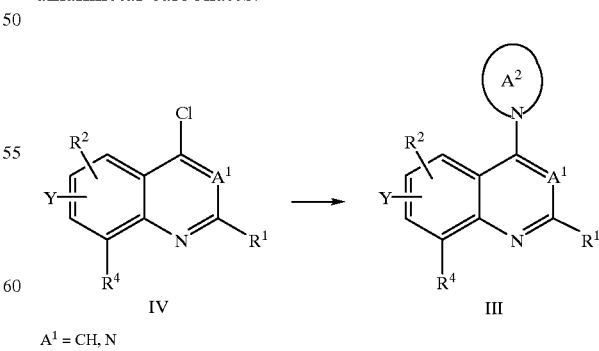

$A^1$ = CH, N

Compounds of formula IV in which $R^1$, $R^2$, $R^4$, $A^1$ and Y have the above significance and can be prepared by reacting a compound of the formula

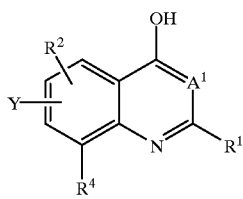

VI with a halogenating agent, preferably phosphorous oxychloride, which may be used in excess as a solvent for the reaction. An aromatic dialkyl amine can also be used as a cosolvent. The reaction is effected at a temperature between 20° C. and the boiling point of the reaction mixture, preferably between 50° C. and 110° C. The aromatic dialkyamine is preferably N,N-dimethylaniline.

Compounds of formula VI, in which $A^1$ is CH, and Y, $R^1$ and $R^2$ have the above significance can be manufactured by reacting a compound of the formula

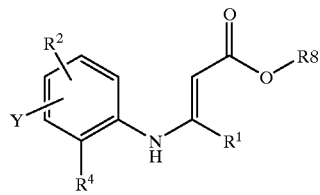

VII wherein $R^1$, $R^2$, $R^4$ and Y are defined as before and $R^8$ represents an alkyl group, preferably methyl or ethyl. This cyclisation reaction is preferably effected in an inert organic solvent such as diphenylether or Dowtherm$^R$ A (Eutetic mixture of 26.5% of diphenyl and 73.5% of diphenylether) at a temperature between about 150° C. and the boiling point of the reaction mixture in such a way that the alcohol formed during the reaction can be distilled out of the reaction mixture.

Compounds of formula VI, wherein $A^1$ is N, and Y, $R^1$, $R^2$ and $R^4$ have the above significance can be prepared by reacting a compound of the formula VIII

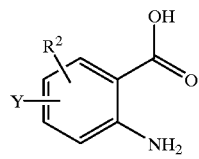

VIII wherein $R^2$, $R^4$ and Y are defined as before. This cyclisation reaction is preferably effected in an inert organic solvent such as absolute dimethylformamide by treating an intermediate VIII with an acylchlorid, preferably acetylchlorid (in the case of $R^1$ is CH$_3$) e.g. in the presence of an organic base, preferably triethylamine at a temperature between 0° C. and 20° C. for a short time, e.g. 20 minutes, followed by heating at 90° C. for some hours, followed by treatment of the reaction mixture with an ammonium salt, preferably ammonium carbonate at a temperature between 20° C. and 100° C. The cyclisation of the anthranilic acid VIII can also be effected by treating VIII in an acid anhydride, preferably acetyl anhydride in the case where $R^1$ is CH$_3$, at a temperature between 20° C. and boiling temperature of the reaction mixture, followed by treatment of the precipitated intermediate with anhydrous ammonia at temperature between −50° C. and −25° C. as described in J. Med. Chem. 1993, 36, 733–746.

Compounds of formula VII, in which $R^1$, $R^2$, $R^4$, Y and $R^8$ have the above significance can be prepared by reacting a compound of formula IX

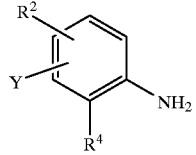

IX in which $R^2$, $R^4$ and Y have the above significance with an appropriate substituted beta-ketoester. The reaction is preferably effected in an inert solvent, e.g. benzene, toluene or cyclohexane at boiling temperature of the reaction mixture. An organic acid, e.g. p-toluensulfonic acid or an inorganic acid, e.g. hydrochlorid acid can be used as a catalyst. The water which is formed during the reaction can be preferably separated from the reaction mixture through azeotropic distillation with e.g. a Dean-Stark water separator. In another variant of the reaction, it is preferably effected in an inert solvent, e.g. benzene, toluene or cyclohexane at room temperature. An organic acid, e.g. p-toluensulfonic acid or an inorganic acid, e.g. hydrochloride acid can be used as a catalyst. The water which is formed during the reaction can be removed from the reaction mixture by treating the reaction mixture with a water-trapping reagent, e.g. molecularsieve.

Compounds of formula VIII, in which $R^2$ and Y have the above significance can be prepared according to S. E. Webber et al. J. Med. Chem. 1993, 36, 733–746.

The conversion of a compound of formula I into a pharmaceutically acceptable salt can be carried out by treatment of such a compound with an inorganic acid, for example a hydrohalic acid, such as, for example, hydrochloric acid or hydrobromic acid, sulfuric acid, nitric acid, phosphoric acid etc., or with an organic acid, such as, for example, acetic acid, citric acid, maleic acid, fumaric acid, tartaric acid, methanesulfonic acid or p-toluenesulfonic acid. The corresponding carboxylate salts can also be prepared from the compounds of formula I by treatment with physiologically compatible bases.

A preferred process for the preparation of a compound of formula I comprises one of the following reactions: the reaction of a compound of formula

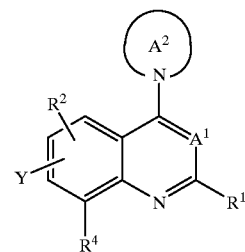

IIIa in the presence of a compound of formula $R^3$-Z            IIa or the reaction of a compound of formula

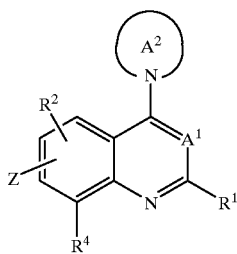
IIIb in the presence of a compound of formula

IIb, wherein $R^1$, $R^2$, $R^3$, $R^4$, $A^1$ and $A^2$ are defined as before and Y and Z are substituents which can be used in transition metal catalyzed cross coupling reactions. In a preferred aspect the reactions a) and b) are performed in the presence of a transition metal complex such as for example a nickel or palladium metal complex, preferably a palladium metal complex, particularly preferred tetrakis-triphenylphosphine-palladium.

In a further preferred embodiment of the reactions a) and b) Y is iodine, bromine, chlorine, methylsulfonyloxy, trifluoromethylsulfonyloxy, phenylsulfonyloxy or p-tosylsulfonyloxy and Z is $(OH)_2B$— or $(R'O)_2B$—, wherein R' is methyl, ethyl, isopropyl or the two R' form together with the oxygen atoms attached to the boron atom a cyclic diester, preferably 1,3-propyldioxy- or 2,3-dimethyl-2,3-butanedioxy, or Z is —$Sn(alkyl)_3$, preferably —$Sn(CH_3)_3$ or —$Sn(n\text{-butyl})_3$, or MgHal or Li or ZnHal, wherein Hal is bromine, iodine or chlorine. Particularly preferred are the above reactions a) and b), wherein Y is bromine. Also particularly preferred are the reactions a) and b), wherein Z is $(OH)_2B$— or —$Sn(Me)_3$.

The invention also includes intermediates of formula X

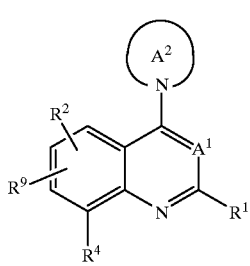
X wherein $R^1$, $R^2$, $R^4$, $A^1$ and $A^2$ are defined as before and, wherein $R^9$ is iodine, bromine, chlorine, methylsulfonyloxy, trifluoromethylsulfonyloxy, phenylsulfonyloxy or p-tosylsulfonyloxy. Particularly preferred are the compounds of formula X, wherein $R^9$ is iodine or bromine.

Especially preferred intermediates of formula X are:
7-iodo-2-methyl-4-pyrrolidin-1-yl-quinoline;
7-iodo-2-methyl-4-piperidin-1-yl-quinoline;
diethyl-(7-iodo-2-methyl-quinolin-4-yl)-amine;
7-iodo-2-methyl-4-morpholin-4-yl-quinoline;
7-iodo-2-methyl-4-(4-methyl-piperazin-1-yl)-quinoline;
4-(3,4-dihydro-1H-isoquinolin-2-yl)-7-iodo-2-methyl-quinoline hydrochloride;
5-iodo-2-methyl-4-piperidin-1-yl-quinoline;
5-iodo-2-methyl-4-pyrrolidin-1-yl-quinoline;
5-iodo-2-methyl-4-morpholin-4-yl-quinoline;
4-azepan-1-yl-7-iodo-2-methyl-quinoline;
6-bromo-2-methyl-4-pyrrolidin-1-yl-quinoline;
7-bromo-4-pyrrolidin-1-yl-quinoline;
7-bromo-2-methyl-4-piperidin-1-yl-quinazoline;
7-bromo-2-methyl-4-pyrrolidin-1-yl-quinazoline;
4-azepan-1-yl-7-bromo-2-methyl-quinazoline;
4-azetidin-1-yl-7-bromo-2-methyl-quinazoline;
7-bromo-4-chloro-2-methyl-quinazoline;
4-chloro-5-iodo-2-methyl-quinoline;
6-bromo-4-chloro-2-methyl-quinoline;
7-bromo-2-methyl-3H-quinazolin-4-one;
3-(3-iodo-phenylamino)-but-2-enoic acid ethyl ester.

Further preferred intermediates of the present invention are:
(7-bromo-2-methyl-quinazolin-4-yl)-dimethyl-amine;
(7-bromo-2-methyl-quinazolin-4-yl)-butyl-amine.

The compounds of formula I described above for use as therapeutically active substances are a further object of the invention.

Also an object of the invention are compounds described above for the production of medicaments for the prophylaxis and therapy of illnesses which are caused by disorders associated with the NPY receptor, particularly for the production of medicaments for the prophylaxis and therapy of arthritis, cardiovascular diseases, diabetes, renal failure and particularly eating disorders and obesity.

Likewise an object of the invention is a pharmaceutical composition containing a compound of formula I described above and a therapeutically inert carrier. Preferred is this composition comprising further a therapeutically effective amount of a lipase inhibitor. Particularly preferred is the above composition, wherein the lipase inhibitor is orlistat.

An object of the invention is also the use of the compounds described above for the production of medicaments, particularly for the treatment and prophylaxis of arthritis, cardiovascular diseases, diabetes, renal failure and particularly eating disorders and obesity.

A further object of the invention comprises compounds which are manufactured according to one of the described processes.

A further object of the invention is a method for the treatment and prophylaxis of arthritis, cardiovascular diseases, diabetes, renal failure and particularly eating disorders and obesity whereby an effective amount of a compound described above is administered.

According to a further aspect of the invention there is provided a method of treatment of obesity in a human in need of such treatment which comprises administration to the human a therapeutically effective amount of a compound according to formula I and a therapeutically effective amount of a lipase inhibitor, particularly preferred, wherein the lipase inhibitor is orlistat. Also subject of the present invention is the mentioned method, wherein the administration is simultaneous, separate or sequential.

A further preferred embodiment of the present invention is the use of a compound of the formula I in the manufacture of a medicament for the treatment and prevention of obesity in a patient who is also receiving treatment with a lipase inhibitor, particularly preferred, wherein the lipase inhibitor is orlistat.

ASSAY PROCEDURES

Cloning of Mouse NPY5 Receptor cDNAs

The full-length cDNA encoding the mouse NPY5 (mNPY5) receptor was amplified from mouse brain cDNA using specific primers, designed based on the published sequence, and Pfu DNA-Polymerase (Stratagene). The amplification product was subcloned into the mammalian expression vector pcDNA3 using Eco RI and XhoI restriction sites. Positive clones were sequenced and one clone, encoding the published sequence was selected for generation of stable cell clones.

Stable Transfection

Human embryonic kidney 293 (HEK293) cells were transfected with 10 μg mNPY5 DNA using the lipofectamine reagent (Gibco BRL) according to the manufacturer's instruction. Two days after transfection, geneticin selection (1 mg/ml) was initiated and several stable clones were isolated. One clone was further used for pharmacological characterization.

Radioligand Competition Binding

Human embryonic kidney 293 cells (HEK293), expressing recombinant mouse NPY5-receptor (mNPY5) were broken by three freeze/thawing cycles in hypotonic Tris buffer (5 mM, pH 7.4, 1 mM $MgCl_2$), homogenized and centrifuged at 72,000×g for 15 min. The pellet was washed twice with 75 mM Tris buffer, pH 7.4, containing 25 mM $MgCl_2$ and 250 mM sucrose, 0.1 mM phenylmethylsulfonylfluoride and 0.1 mM 1,10-pheneanthrolin, resuspended in the same buffer and stored in aliquots at −80° C. Protein was determined according to the method of Lowry using bovine serum albumine (BSA) as a standard.

Radioligand competition binding assays were performed in 250 μl 25 mM Hepes buffer (pH 7.4, 2.5 mM $CaCl_2$, 1 mM $MgCl_2$, 1% bovine serum albumine, and 0.01% $NaN_3$ containing 5 μg protein, 100 pM [$^{125}$I]labelled peptide YY (PYY) and 10 μL DMSO containing increasing amounts of unlabelled test compounds. After incubation for 1 h at 22° C., bound and free ligand are separated by filtration over glass fibre filters. Non specific binding is assessed in the presence of 1 μM unlabelled PYY. Specific binding is defined as the difference between total binding and non specific binding. $IC_{50}$ values are defined as the concentration of antagonist that displaces 50% of the binding of [$^{125}$I] labelled neuropeptide Y. It is determined by linear regression analysis after logit/log transformation of the binding data.

Results obtained in the foregoing test using representative compounds of the invention as the test compounds are shown in the following table:

| Compound | $IC_{50}$ |
| --- | --- |
| 7-(4-methoxy-phenyl)-2-methyl-4-pyrrolidin-1-yl-quinoline (example 1.6) | 0.06 micro Molar |
| 7-(1H-indol-5-yl)-2-methyl-4-piperidin-1-yl-quinoline (example 1.17) | 0.10 micro Molar |

Preferred compounds as described above have $IC_{50}$ values below 1000 nM; more preferred compounds have $IC_{50}$ values below 100 nM, particularly below 10 nM. Most preferred compounds have $IC_{50}$ values below 1 nM. These results have been obtained by using the foregoing test.

The compounds of formula I and their pharmaceutically acceptable salts, solvates and esters can be used as medicaments (e.g. in the form of pharmaceutical preparations). The pharmaceutical preparations can be administered internally, such as orally (e.g. in the form of tablets, coated tablets, dragées, hard and soft gelatin capsules, solutions, emulsions or suspensions), nasally (e.g. in the form of nasal sprays) or rectally (e.g. in the form of suppositories). However, the administration can also be effected parentally, such as intramuscularly or intravenously (e.g. in the form of injection solutions).

The compounds of formula I and their pharmaceutically acceptable salts, solvates and esters can be processed with pharmaceutically inert, inorganic or organic adjuvants for the production of tablets, coated tablets, dragées and hard gelatin capsules. Lactose, corn starch or derivatives thereof, talc, stearic acid or its salts etc. can be used, for example, as such adjuvants for tablets, dragées and hard gelatin capsules.

Suitable adjuvants for soft gelatin capsules, are, for example, vegetable oils, waxes, fats, semi-solid substances and liquid polyols, etc.

Suitable adjuvants for the production of solutions and syrups are, for example, water, polyols, saccharose, invert sugar, glucose, etc.

Suitable adjuvants for injection solutions are, for example, water, alcohols, polyols, glycerol, vegetable oils, etc.

Suitable adjuvants for suppositories are, for example, natural or hardened oils, waxes, fats, semi-solid or liquid polyols, etc.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

In accordance with the invention the compounds of formula I and their pharmaceutically acceptable salts, solvates and esters can be used for the prophylaxis and treatment of arthritis, cardiovascular diseases, diabetes, renal failure and particularly eating disorders and obesity. The dosage can vary in wide limits and will, of course, be fitted to the individual requirements in each particular case. In general, in the case of oral administration a daily dosage of about 0.1 mg to 20 mg per kg body weight, preferably about 0.5 mg to 4 mg per kg body weight (e.g. about 300 mg per person), divided into preferably 1–3 individual doses, which can consist, for example, of the same amounts, should be appropriate. It will, however, be clear that the upper limit given above can be exceeded when this is shown to be indicated.

The invention is illustrated hereinafter by Examples, which have no limiting character.

EXAMPLES

Example 1.1

Preparation of 7-(3-chloro-phenyl)-2-methyl-4-pyrrolidin-1-yl-quinoline:

A mixture of 1.5 g 7-iodo-2-methyl-4-pyrrolidin-1-yl-quinoline (Example 3.1), 256 tetrakis(triphenylphosphine) palladium and 30 ml Dimethoxyethane is stirred under argon for 15 min. 1.04 g 3-Chlorophenylboronic acid and 7 ml Ethanol are added. The resulting red solution is stirred for another 10 min. at room temperature and treated afterwards with 19 ml of a 2M aqueous solution of sodium carbonate. The mixture is refluxed for 1.5 h under vigorous stirring. After the reaction is complete, the reaction mixture is concentrated on a rotary evaporator. The residue is taken up in 50 ml water and extracted twice with 50 ml ethyl acetate. The combined organic phases are washed with 50 ml saturated aqueous solution of sodium chloride, dried over magnesium sulfate and filtered. The filtrate is evaporated and the residue is chromatographed on silica gel (eluent: Dichloromethane/Methanol 19:1 then 4:1). The pure fractions are combined and evaporated. 1.235 g of 7-(3-Chloro-phenyl)-2-methyl-4-pyrrolidin-1-yl-quinoline are obtained as a colorless oil. MS (ISP): 323.3 (M+H)$^+$.

The following compounds were prepared in analogy to Example 1.1.:

Example 1.2

In analogy with Example 1.1) with 3-trifluoromethylphenylboronic acid there is obtained 2-Methyl-4-pyrrolidin-1-yl-7-(3-trifluoromethyl-phenyl)-quinoline as a yellowish foam. MS (ISP): 357.3 (M+H)$^+$.

Example 1.3

In analogy with Example 1.1) with 3-aminophenylboronic acid there is obtained 3-(2-Methyl-4-pyrrolidin-1-yl-quinolin-7-yl)-phenylamine as a beige foam. MS (EI): peaks at m/e: 303 (M+, 100%), 274 (14%), 260 (9%).

Example 1.4

In analogy with Example 1.1) with 4-acetylphenylboronic acid there is obtained 1-[4-(2-methyl-4-pyrrolidin-1-yl-quinolin-7-yl)-phenyl]-ethanone as a slightly brown foam. MS (ISP): 331.3 (M+H)$^+$.

Example 1.5

In analogy with Example 1.1) with phenylboronic acid there is obtained 2-methyl-7-phenyl-4-pyrrolidin-1-yl-quinoline as a yellowish foam. MS (ISP): 289.3 (M+H)$^+$.

Example 1.6

In analogy with Example 1.1) with 4-methoxyphenylboronic acid there is obtained 7-(4-methoxy-phenyl)-2-methyl-4-pyrrolidin-1-yl-quinoline as a white foam. MS (ISP): 319.4 (M+H)$^+$.

Example 1.7

In analogy with Example 1.1) with 2-thiopheneboronic acid there is obtained 2-methyl-4-pyrrolidin-1-yl-7-thiophen-2-yl-quinoline as a beige foam. MS (ISP): 295.3 (M+H)$^+$.

Example 1.8

In analogy with Example 1.1) with pyridine-3-boronic acid 1,3-propane-diol cyclic ester there is obtained 2-Methyl-7-pyridin-3-yl-4-pyrrolidin-1-yl-quinoline as a yellowish foam. MS (ISP): 290.3 (M+H)$^+$.

Example 1.9

In analogy with Example 1.1) with 5-pyrimidinylboronic acid (Chem. Scr. 1986, 26, 305–309) there is obtained 2-methyl-7-pyrimidin-5-yl-4-pyrrolidin-1-yl-quinoline as a light yellow solid. MS (ISP): 290.3 (M+H)$^+$.

Example 1.10

In analogy with Example 1.1) with 3-trifluoromethylphenylboronic acid and 7-iodo-2-methyl-4-piperidin-1-yl-quinoline (Example 3.2) there is obtained 2-methyl-4-piperidin-1-yl-7-(3-trifluoromethyl-phenyl)-quinoline as a yellow foam. MS (ISP): 371.3 (M+H)$^+$.

Example 1.11

In analogy with Example 1.1) with 3-Chlorophenylboronic acid and 7-iodo-2-methyl-4-piperidin-1-yl-quinoline (Example 3.2) there is obtained 7-(3-chloro-phenyl)-2-methyl-4-piperidin-1-yl-quinoline as a yellow foam. MS (EI): peaks at m/e: 337 (M+, 45%), 335(100%), 279 (9%).

Example 1.12

In analogy with Example 1.1) with 4-acetylphenylboronic acid and and 7-Iodo-2-methyl-4-piperidin-1-yl-quinoline (Example 3.2) there is obtained 1-[4-(2-methyl-4-piperidin-1-yl-quinolin-7-yl)-phenyl]-ethanone as a yellow foam. MS (ISP): 345.4 (M+H)$^+$.

Example 1.13

In analogy with Example 1.1) with 3-aminophenylboronic acid and 7-iodo-2-methyl-4-piperidin-1-yl-quinoline (Example 3.2) there is obtained 3-(2-methyl-4-piperidin-1-yl-quinolin-7-yl)-phenylamine as a slightly brown solid. MS (EI): peaks at m/e: 317 (M+, 100%), 260 (8%), 234 (9%).

Example 1.14

In analogy with Example 1.1) with 4-methoxyphenylboronic acid and 7-iodo-2-methyl-4-piperidin-1-yl-quinoline (Example 3.2) there is obtained 7-(4-methoxy-phenyl)-2-methyl-4-piperidin-1-yl-quinoline as a slightly orange foam. MS (ISP): 333.3(M+H)$^+$.

Example 1.15

In analogy with Example 1.1) with 2-thiophenboronic acid and 7-iodo-2-methyl-4-piperidin-1-yl-quinoline (Example 3.2) there is obtained 2-methyl-4-piperidin-1-yl-7-thiophen-2-yl-quinoline as a yellow solid. Mp. 122–123° C. MS (ISP): 309.2(M+H)$^+$.

Example 1.16

In analogy with Example 1.1) with phenylboronic acid and 7-iodo-2-methyl-4-piperidin-1-yl-quinoline (Example 3.2) there is obtained 2-methyl-7-phenyl-4-piperidin-1-yl-quinoline as a yellow solid. Mp. 111–112° C. MS (EI): peaks at m/e: 302 (M+, 100%), 245 (12%), 219(10%).

Example 1.17

In analogy with Example 1.1) with 1H-indol-5-ylboronic acid (Heterocycles, 1992, 34, 1169–1175) and 7-iodo-2-methyl-4-piperidin-1-yl-quinoline (Example 3.2) there is obtained 7-(1H-Indol-5-yl)-2-methyl-4-piperidin-1-yl-quinoline as a slightlybrown solid. MS (ISP): 342.3(M+H)$^+$.

Example 1.18

In analogy with Example 1.1) with pyridine-3-boronic acid 1,3-propanediol cyclic ester and 7-iodo-2-methyl-4-piperidin-1-yl-quinoline (Example 3.2) there is obtained 2-methyl-4-piperidin-1-yl-7-pyridin-3-yl-quinoline as a yellow foam. MS (ISP): 304.3(M+H)$^+$.

Example 1.19

In analogy with Example 1.1) with 3-trifluoromethylphenylboronic acid and diethyl-(7-iodo-2-methyl-quinolin-4-yl)-amine (Example 3.3) there is obtained diethyl-[2-methyl-7-(3-trifluoromethyl-phenyl)-quinolin-4-yl]-amine as a colorless oil. MS (ISP): 359.2(M+H)$^+$.

Example 1.20

In analogy with Example 1.1) with 3-aminophenylboronic acid and diethyl-(7-iodo-2-methyl-quinolin-4-yl)-amine (Example 3.3) there is obtained [7-(3-amino-phenyl)-2-methyl-quinolin-4-yl]-diethyl-amine as a slightly orange oil. MS (ISP): 306.3(M+H)+.

Example 1.21

In analogy with Example 1.1) with 4-acetylphenylboronic acid and diethyl-(7-iodo-2-methyl-quinolin-4-yl)-amine (Example 3.3) there is obtained 1-[4-(4-diethylamino-2-methyl-quinolin-7-yl)-phenyl]-ethanone as a slightly orange oil. MS (ISP): 333.3(M+H)+.

Example 1.22

In analogy with Example 1.1) with 3-trifluoromethylphenylboronic acid and 7-Iodo-2-methyl-4-morpholin-4-yl-quinoline (Example 3.4) there is obtained 2-methyl-4-morpholin-4-yl-7-(3-trifluoromethyl-phenyl)-quinoline as a yellow foam. MS (EI): peaks at m/e: 372 (M+, 100%), 314 (67%), 169(19%).

Example 1.23

In analogy with Example 1.1) with 4-acetylphenylboronic acid and 7-iodo-2-methyl-4-morpholin-4-yl-quinoline (Example 3.4) there is obtained 1-[4-(2-methyl-4-morpholin-4-yl-quinolin-7-yl)-phenyl]-ethanone as a slightly red foam. MS (ISP): 347.3(M+H)+.

Example 1.24

In analogy with Example 1.1) with 3-trifluoromethylphenylboronic acid and 7-iodo-2-methyl-4-(4-methyl-piperazin-1-yl)-quinoline (Example 3.5) there is obtained 2-methyl-4-(4-methyl-piperazin-1-yl)-7-(3-trifluoromethyl-phenyl)-quinoline as an orange foam. MS (EI): peaks at m/e: 385(M+, 57%), 370 (19%), 42(100%).

Example 1.25

In analogy with Example 1.1) with 3-trifluoromethylphenylboronic acid and 4-(3,4-dihydro-1H-isoquinolin-2-yl)-7-iodo-2-methyl-quinoline hydrochloride (Example 3.6) there is obtained 4-(3,4-dihydro-1H-isoquinolin-2-yl)-2-methyl-7-(3-trifluoromethyl-phenyl)-quinoline as a light-yellow foam. MS (ISP): 419.3(M+H)+.

Example 1.26

In analogy with Example 1.1) with 3-chlorophenylboronic acid and 5-iodo-2-methyl-4-piperidin-1-yl-quinoline (Example 3.7) there is obtained 5-(3-chloro-phenyl)-2-methyl-4-piperidin-1-yl-quinoline as a colourless viscous oil. MS (EI): peaks at m/e: 336(M+, 100%), 307 (17%), 277(32%), 225 (49%).

Example 1.27

In analogy with Example 1.1) with 3-trifluoromethylphenylboronic acid and 5-iodo-2-methyl-4-piperidin-1-yl-quinoline (Example 3.7) there is obtained 2-methyl-4-piperidin-1-yl-5-(3-trifluoromethyl-phenyl)-quinoline as a yellow foam. MS (ISP): 371.4(M+H)+.

Example 1.28

In analogy with Example 1.1) with 3-chlorophenylboronic acid and 5-iodo-2-methyl-4-pyrrolidin-1-yl-quinoline (Example 3.8) there is obtained 5-(3-chloro-phenyl)-2-methyl-4-pyrrolidin-1-yl-quinoline as a light-yellow amorphous solid. MS (ISP): 323.3(M+H)+.

Example 1.29

In analogy with Example 1.1) with 3-chlorophenylboronic acid and 5-Iodo-2-methyl-4-morpholin-1-yl-quinoline (Example 3.9) there is obtained 5-(3-chloro-phenyl)-2-methyl-4-morpholin-4-yl-quinoline as a colorless viscous oil. MS (EI): peaks at m/e: 338(M+, 87%), 277(100%), 245 (37%).

Example 1.30

In analogy with Example 1.1) with 3-trifluoromethylphenylboronic acid and 4-azepan-1-yl-7-iodo-2-methyl-quinoline (Example 3.10) there is obtained 4-azepan-1-yl-2-methyl-7-(3-trifluoromethyl-phenyl)-quinoline as a yellowish foam. MS (ISP): 385.3 (M+H)+.

Example 1.31

In analogy with Example 1.1) with 3-chlorophenylboronic acid and 6-bromo-2-methyl-4-pyrrolidin-1-yl-quinoline (Example 3.11) there is obtained 6-(3-chloro-phenyl)-2-methyl-4-pyrrolidin-1-yl-quinoline as a yellowish gum. MS (ISP): 323.3 (M+H)+.

Example 1.32

In analogy with Example 1.1) with 3-chlorophenylboronic acid and 7-bromo-4-pyrrolidin-1-yl-quinoline (Example 3.12) there is obtained 7-(3-chloro-phenyl)-4-pyrrolidin-1-yl-quinoline as a beige amorphous solid. MS (ISP): 309.2 (M+H)+.

Example 2.1

Preparation of 2-Methyl-4-piperidin-1-yl-7-(3-trifluoromethyl-phenyl)-quinazoline:

In analogy with Example 1.1) with 3-trifluoromethylphenylboronic acid and 7-bromo-2-methyl-4-piperidin-1-yl-quinazoline (Example 4.1) there is obtained 2-methyl-4-piperidin-1-yl-7-(3-trifluoromethyl-phenyl)-quinazoline as a light-yellow solid. MS (EI): peaks at m/e: 371(M+, 76%), 342 (100%), 288(57%).

Example 2.2

In analogy with Example 1.1) with 4-methoxyphenylboronic acid and 7-bromo-2-methyl-4-piperidin-1-yl-quinazoline (Example 4.1) there is obtained 7-(4-methoxy-phenyl)-2-methyl-4-piperidin-1-yl-quinazoline as a light-yellow oil. MS (ISP): 434.3(M+H)+.

Example 2.3

In analogy with Example 1.1) with 3-aminophenylboronic acid and 7-bromo-2-methyl-4-piperidin-1-yl-quinazoline (Example 4.1) there is obtained 3-(2-methyl-4-piperidin-1-yl-quinazolin-7-yl)-phenylamine as a light-yellow solid. MS (ISP): 319.4(M+H)+.

Example 2.4

In analogy with Example 1.1) with pyridine-3-boronic acid 1,3-propanediol cyclic ester and 7-bromo-2-methyl-4-piperidin-1-yl-quinazoline (Example 4.1) there is obtained 2-methyl-4-piperidin-1-yl-7-pyridin-3-yl-quinazoline as a light-yellow solid. MS (ISP): 305.3(M+H)+.

Example 2.5

In analogy with Example 1.1) with 5-Pyrimidinylboronic acid (Chem. Scr. 1986, 26, 305–309) and 7-bromo-2- methyl-4-pyrrolidin-1-yl-quinazoline (Example 4.2) there is obtained 2-methyl-7-pyrimidin-5-yl-4-pyrrolidin-1-yl-quinazoline as a light-yellow solid. MS (ISP): 292.3(M+H)$^+$.

Example 2.6

In analogy with example 1.1) with 3-trifluoromethylphenylboronic acid and 7-bromo-2-methyl-4-pyrrolidin-1-yl-quinazoline (Example 4.2) there is obtained 2-methyl-4-pyrrolidin-1-yl-7-(3-trifluoromethylphenyl)-quinazoline as a light-yellow foam. MS (ISP): 358.2 (M+H)$^+$.

Example 2.7

In analogy with example 1.1) with 3-chlorophenyl boronic acid and 7-bromo-2-methyl-4-pyrrolidin-1-yl-quinazoline (Example 4.2) there is obtained 7-(3-chlorophenyl)-2-methyl-4-pyrrolidin-1-yl-quinazoline as a white solid. MS (ISP): 324.3(M+H)$^+$.

Example 2.8

In analogy with example 1.1) with 3-chlorophenyl boronic acid and 7-bromo-2-methyl-4-piperidin-1-yl-quinazoline (Example 4.1) there is obtained 7-(3-chlorophenyl)-2-methyl-4-piperidin-1-yl-quinazoline as a light-yellow solid. MS (ISP): 338.2(M+H)$^+$.

Example 2.9

In analogy with example 1.1) with 3-trifluoromethylphenylboronic acid and 4-azepan-1-yl-7-bromo-2-methyl-quinazoline (Example 4.3) there is obtained 4-azepan-1-yl-2-methyl-7-(3-trifluoromethylphenyl)-quinazoline as an off-white amorphous solid. MS (ISP): 386.3(M+H)$^+$.

Example 3.1

Preparation of 7-iodo-2-methyl-4-pyrrolidin-1-yl-quinoline:

A suspension of 2 g of 4-chloro-7-iodo-2-methyl-quinoline (European patent application EP 0497371, CA 143946-47-8) in 20 ml absolute ethanol is treated successively with 1.09 ml pyrrolidine, 0.2 ml pyridine and 50 mg potassium iodide under argon. The resulting mixture is refluxed for 24 h. The solvent is then distilled off. The residue is taken up in 50 ml water and basified to pH 12 with a 2N solution of sodium hydroxyde. The solid is filtered upon precipitation and washed with 20 ml of water and 20 ml of diethylether. The final product is dried under vacuum yielding 1.95 g (87%) of 7-iodo-2-methyl-4-pyrrolidin-1-yl-quinoline as an off-white solid. Mp: 99–102° C. MS (EI): peaks at m/e: 338(M+, 100%), 296 (5%), 183(9%).

Example 3.2

In analogy with Example 3.1) with 4-chloro-7-iodo-2-methyl-quinoline and piperidine there is obtained 7-iodo-2-methyl-4-piperidin-1-yl-quinoline as a light-yellowish solid. Mp. 124–126° C. MS (EI): peaks at m/e: 352(M+, 100%), 296 (4%), 269(5%).

Example 3.3

In analogy with Example 3.1) with 4-chloro-7-iodo-2-methyl-quinoline and diethylamine in an autoclave for 120 h at 150° C. there is obtained diethyl-(7-iodo-2-methyl-quinolin-4-yl)-amine as a reddish oil. MS (EI): peaks at m/e: 339(M+, 100%), 325 (73%), 198(43%).

Example 3.4

In analogy with Example 3.1) with 4-chloro-7-iodo-2-methyl-quinoline and morpholine there is obtained 7-iodo-2-methyl-4-morpholin-4-yl-quinoline as an off-white solid. Mp. 103–105° C. MS (EI): peaks at m/e: 354(M+, 100%), 296 (73%), 169(13%)

Example 3.5

In analogy with Example 3.1) with 4-chloro-7-iodo-2-methyl-quinoline and N-methylpiperazine there is obtained 7-iodo-2-methyl-4-(4-methyl-piperazin-1-yl) quinoline as a light-brownish solid. Mp. 92–94° C. MS (EI): peaks at m/e: 367(M+, 100%), 352 (38%), 310(11%).

Example 3.6

In analogy with Example 3.1) with 4-chloro-7-iodo-2-methyl-quinoline and tetrahydroisoquinoline there is obtained 4-(3,4-dihydro-1H-isoquinolin-2-yl)-7-iodo-2-methyl-quinoline hydrochloride as a beige solid. Mp.>230° C. MS (ISP): 401.3(M+H)$^+$.

Example 3.7

In analogy with Example 3.1) with 4-chloro-5-iodo-2-methyl-quinoline (Example 5.2) and piperidine there is obtained 5-iodo-2-methyl-4-piperidin-1-yl-quinoline as an orange oil. MS (ISP): 353.2(M+H)$^+$.

Example 3.8

In analogy to Example 3.1) with 4-chloro-5-iodo-2-methyl-quinoline and pyrrolidine there is obtained 5-iodo-2-methyl-4-pyrrolidin-1-yl-quinoline as a light-yellow solid. Mp. 97–99° C. MS (ISP): 339.1(M+H)$^+$.

Example 3.9

In analogy to Example 3.1) with 4-chloro-5-iodo-2-methyl-quinoline and morpholine there is obtained 5-iodo-2-methyl-4-morpholin-4-yl-quinoline as a yellow solid. Mp. 144–145° C. MS (ISP): 355.1(M+H)$^+$.

Example 3.10

In analogy with Example 3.1) with 4-chloro-7-iodo-2-methyl-quinoline and azepine there is obtained 4-azepan-1-yl-7-iodo-2-methyl-quinoline as a beige solid. Mp.>90–93° C. MS (ISP): 367.1(M+H)$^+$.

Example 3.11

In analogy with Example 3.1) with 6-bromo-4-chloro-2-methyl-quinoline (Example 5.3) and pyrrolidine there is obtained 6-bromo-2-methyl-4-pyrrolidin-1-yl-quinoline as a beige solid. MS (ISP): 291.2(M+H)$^+$.

Example 3.12

In analogy with Example 3.1) with 7-bromo-4-chloro-quinoline (J. Amer. Chem. Soc. 1946, 68, 113–116)and pyrrolidine there is obtained 7-bromo-4-pyrrolidin-1-yl-quinoline as a beige solid. MS (ISP): 277.2(M+H)$^+$.

Example 4.1

Preparation of 7-bromo-2-methyl-4-piperidin-1-yl-quinazoline:

In analogy to Example 3.1) with 7-bromo-4-chloro-2-methyl-quinazoline (Example 5.1) and piperidine there is obtained 7-bromo-2-methyl-4-piperidin-1-yl-quinazoline as an amorphous yellow solid. MS (ISP): 306.2(M+H)$^+$.

Example 4.2

In analogy to Example 3.1) with 7-bromo-4-chloro-2-methyl-quinazoline (Example 5.1) and pyrrolidine there is obtained 7-bromo-2-methyl-4-pyrrolidin-1-yl-quinazoline as a yellow solid. Mp. 120–122° C. MS (ISP): 292.2(M+H)$^+$.

Example 4.3

In analogy to Example 3.1) with 7-bromo-4-chloro-2-methyl-quinazoline (Example 5.1) and azepine there is obtained 4-azepan-1-yl-7-bromo-2-methyl-quinazoline as an orange oil. MS (ISP): 320.3(M+H)$^+$.

Example 4.4

In analogy to Example 3.1) with 7-bromo-4-chloro-2-methyl-quinazoline (Example 5.1) and azetidine there is obtained 4-azetidin-1-yl-7-bromo-2-methyl-quinazoline as a light-brown solid. Mp. 129–131° C. MS (ISP): 278.1(M+H)$^+$.

Example 4.5

In analogy to Example 3.1) with 7-bromo-4-chloro-2-methyl-quinazoline (Example 5.1) and dimethylamine there is obtained (7-bromo-2-methyl-quinazolin-4-yl)-dimethyl-amine as a brown solid. Mp. 55–57° C. MS (ISP): 266.2 (M+H)$^+$.

Example 4.6

In analogy to Example 3.1) with 7-bromo-4-chloro-2-methyl-quinazoline (Example 5.1) and n-butylamine there is obtained (7-bromo-2-methyl-quinazolin-4-yl)-butyl-amine as a beige solid. Mp. 133–135° C. MS (ISP): 294.2(M+H)$^+$.

Example 5.1
Preparation of 7-bromo-4-chloro-2-methyl-quinazoline:

A suspension of 0.45 g 7-bromo-2-methyl-3H-quinazolin-4-one in 0.48 ml N,N-dimethylaniline is treated with 1.41 ml phosphourous oxychloride and heated at 60° C. for 2 h. The reaction mixture is evaporated in vacuo and the residue is taken up with 20 ml water, neutralized with 10 ml saturated aqueous sodium bicarbonate and extracted with 25 ml dichloromethane twice. The organic layer is washed with 25 ml water, 25 ml brine, dried over magnesium sulfate and evaporated in vacuo. The residue is purified by chromatography on silica gel with Heptane/ethylacetate 2:1. 0.288 g (59%) of 7-bromo-4-chloro-2-methyl-quinazoline are obtained as an orange solid. Mp.>82° C. (dec). MS (EI): peaks at m/e: 258(M+, 37%), 221 (100%), 179(9%).

Example 5.2
Preparation of 4-chloro-5-iodo-2-methyl-quinoline 25 g of crude 3-(3-Iodo-phenylamino)-but-2-enoic acid ethyl ester (Example 7.1) is added rapidly to 25 ml boiling Dowtherm A, keeping the internal temperature above 250° C. After 1.5 h of reaction time, the mixture is cooled at room temperature. The solid which separates is filtered, washed with 50 ml dichloromethane and dried in vacuo to obtain 17.27 g (83.6%) of a mixture of 7-iodo-2-methyl-quinolin-4-ol and 5-iodo-2-methyl-quinolin-4-ol. To 17.27 g of the above product is added 20 ml phosphorous oxychloride. The resulting suspension is stirred at room temperature for 2 h. The crystalline product is triturated with 50 ml dry diethyl-ether and filtered. The cake is suspended in 50 ml ice water and concentrated ammonium hydroxide is added until the resulting suspension is permanently basic. The product is filtered, washed with 50 ml water and dried in vacuo. Purification of the crude product by chromatography on silica gel with Heptane/ethylacetate 2:1 gives 7.1 g (41%) of 4-chloro-7-iodo-2-methyl-quinoline and 4.26 g (23%) of 4-chloro-5-iodo-2-methyl-quinoline as a beige solid. Mp. 98–100° C. MS (EI): peaks at m/e: 303 (M+, 100%), 176 (100%), 140(21%).

Example 5.3

In analogy with Example 5.1) with 6-bromo-4-hydroxy-2-methyl-quinoline (Synthesis, 1987, 482–483) there is obtained 6-Bromo-4-chloro-2-methyl-quinoline as a light-purple solid. MS (EI): peaks at m/e: 256(M+, 100%), 220 (13%), 141(20%).

Example 6.1
Preparation of 7-bromo-2-methyl-3H-quinazolin-4-one:

To a solution of 0.81 g 4-bromoanthranilic acid (J. Org. Chem. 1997, 62, 1240–1256), 39 mg 4-(dimethylamino)pyridine and 2.09 ml triethylamine in dry dimethylformamide is added dropwise 0.69 ml acetylchloride at 3° C. for 20 min. in an ice-water bath under argon. The reaction mixture is then heated at 90° C. for 3 h. and 1.08 g ammonium carbonate is added portionwise over 10 min., and the mixture is stirred at the same temperature for 1 h. After cooling, the mixture is poured onto 20 ml water and the precipitate is filtered, washed with water and dried in vacuo to give 0.46 g (51%) of crude 7-Bromo-2-methyl-3H-quinazolin-4-one as a light-brown solid. Mp.>191° C. (dec.). MS (EI): peaks at m/e: 240(M+, 100%), 223 (14%), 197(18%).

Example 7.1
Preparation of 3-(3-iodo-phenylamino)-but-2-enoic acid ethyl ester:

A mixture of 47.79 g 3-iodoaniline, 27.7 ml ethyl acetoacetate and 0.13 ml 37% hydrochlorid acid in 65 ml benzene is boiled under a reflux condenser fitted with a water separator. After 4 h. 4 ml of water have been collected. The solvent is removed at reduced pressure and the residual oil dried in vacuo 3-(3-iodo-phenylamino)-but-2-enoic acid ethyl ester is obtained as a light brown oil. MS (ISP): 332.1 (M+H)$^+$.

Example 8.1

Preparation of 7-(4-Methoxy-phenyl)-2-methyl-4-pyrrolidin-1-yl-quinazoline; Compound with Formic Acid:

To a solution of 44 mg (0.15 mmol) 7-Bromo-2-methyl-4-pyrrolidin-1-yl-quinazoline in 1.2 ml dioxane/dimethoxyethane 1:1 was added 57 mg (0.375 mmol) 4-methoxy-phenyl-boronic acid in 0.4 ml ethanol, 7 mg (0.007 mmol) Dichloro[1,1'-Bis(diphenylphosphino)-ferrocene]-palladium (II) dichloromethan adduct, and 0.6 ml 2 M Na$_2$CO$_3$aq. and the mixture was heated to 85° C. for 12 h. After filtration, the mixture was purified by reversed phase column chromatography eluting with an acetonitrile/water (formic acid) gradient yielding 17 mg (35%) of the title compound. MS m/e (%): 320.4 (M+H$^+$, 100).

According to example 8.1 further quinazoline derivatives have been synthesised. The results are compiled in the following list comprising example 8.2 to example 8.15. The isolated formiates 8.1–8.15 can each be transferred to the respective parent compound by treatment with base.

The examples 8.2–8.15 have each been synthesised from 7-Bromo-2-methyl-4-pyrrolidin-1-yl-quinazoline and the respective boronic acid or the 4,4,5,5-tetramethyl-1,3,2-dioxaborolan-2-yl-derivative thereof comprised in the following table:

| Ex. | Boronic acid of the 4,4,5,5-tetramethyl-1,3,2-dioxaborolan-2-yl-derivative thereof | Product Name | MH+ found |
|---|---|---|---|
| 8.2 | 4,4,5,5-Tetramethyl-2-thiophen-3-yl-[1,3,2]dioxaborolane (Lit.: WO 0027853A1) | 2-Methyl-4-pyrrolidin-1-yl-7-thiophen-3-yl-quinazoline; compound with formic acid | 296.4 |
| 8.3 | [4-(4,4,5,5-Tetramethyl-[1,3,2]dioxaborolan-2-yl)-phenyl]-carbamic acid tert-butyl ester (Lit.: WO 0119829A2, CSIRO, Molecular Science, Clayton South VIC 3169, Australia) | [4-(2-Methyl-4-pyrrolidin-1-yl-quinazolin-7-yl)-phenyl]-carbamic acid tert-butyl ester; compound with formic acid | 405.5 |
| 8.4 | 3-(4,4,5,5-Tetramethyl-[1,3,2]dioxaborolan-2-yl)-benzonitrile (Lit.: WO 9845265A1) | 3-(2-Methyl-4-pyrrolidin-1-yl-quinazolin-7-yl)-benzonitrile; compound with formic acid | 315.4 |
| 8.5 | 3,5-Dichloro-benzeneboronic acid (commercially available) | 7-(3,5-Dichloro-phenyl)-2-methyl-4-pyrrolidin-1-yl-quinazoline; compound with formic acid | 359.3 |
| 8.6 | 3-Acetylphenylboronic acid (commercially available) | 1-[3-(2-Methyl-4-pyrrolidin-1-yl-quinazolin-7-yl)-phenyl]-ethanone; compound with formic acid | 332.4 |
| 8.7 | 4-Trifluoromethylphenyl-boronic acid (commercially available) | 2-Methyl-4-pyrrolidin-1-yl-7-(4-trifluoromethyl-phenyl)-quinazoline; compound with formic acid | 358.4 |
| 8.8 | Thiophene-2-boronic acid (commercially available) | 2-Methyl-4-pyrrolidin-1-yl-7-thiophen-2-yl-quinazoline; compound with formic acid | 296.4 |
| 8.9 | 5-Acety-2-thiopheneboronic acid (commercially available) | 1-[5-(2-Methyl-4-pyrrolidin-1-yl-quinazolin-7-yl)-thiophen-2-yl]-ethanone; compound with formic acid | 338.4 |
| 8.10 | 5-(4,4,5,5-Tetramethyl-[1,3,2]dioxaborolan-2-yl)-1H-indole (Lit.: WO 0027853A1) | 7-(1H-Indol-5-yl)-2-methyl-4-pyrrolidin-1-yl-quinazoline | 329.4 |
| 8.11 | N-[2-Methyl-4-(4,4,5,5-tetramethyl-[1,3,2]dioxaborolan-2-yl)-phenyl]-acetamide (Lit.: WO 0027853A1) | N-[2-Methyl-4-(2-methyl-4-pyrrolidin-1-yl-quinazolin-7-yl)-phenyl]-acetamide; compound with formic acid | 361.5 |
| 8.12 | 3-Nitrophenylboronic acid (commercially available) | Formic acid; 2-methyl-7-(3-nitro-phenyl)-4-pyrrolidin-1-yl-quinazoline | 335.4 |
| 8.13 | 3-(4,4,5,5-Tetramethyl-[1,3,2]dioxaborolan-2-yl)-phenylamine (WO 9831688A1) | 3-(2-Methyl-4-pyrrolidin-1-yl-quinazolin-7-yl)-phenylamine; compound with formic acid | 305.4 |
| 8.14 | 3-(4,4,5,5-Tetramethyl-[1,3,2]dioxaborolan-2-yl)-phenol (commercially available) | 3-(2-Methyl-4-pyrrolidin-1-yl-quinazolin-7-yl)-phenol; compound with formic acid | 306.4 |
| 8.15 | (3-Trifluoromethoxy)-benzeneboronic acid (commercially available) | 2-Methyl-4-pyrrolidin-1-yl-7-(3-trifluoromethoxy-phenyl)-quinazoline; compound with formic acid | 374.4 |

Example 9.1
2-Methyl-7-phenyl-4-pyrrolidin-1-yl-quinoline; Compound with Formic Acid:

To a solution of 43 mg (0.13 mmol) 7-Iodo-2-methyl-4-pyrrolidin-1-yl-quinoline in 1.2 ml dioxane/dimethoxyethane 1:1 was added 39.6 mg (0.325 mmol) phenyl-boronic acid, 6 mg (0.007 mmol) Dichloro[1,1'-Bis(diphenylphosphino)-ferrocene]palladium (II) dichloromethan adduct, and 0.55 ml 2M $Na_2CO_3$aq. and the mixture was heated to 85° C. for 12 h. After filtration the mixture was purified by reversed phase column chromatography eluting with an acetonitrile/water (formic acid) gradient yielding 25 mg (57%) of the title compound. MS m/e (%): 289.4 ($MH^+$, 100).

According to example 9.1 further quinoline derivatives have been synthesised. The results are compiled in the following table No 2 comprising example 9.2 to example 9.39. The isolated formiates 9.1–9.39 can each be transferred to the respective parent compound by treatment with base.

The examples 9.2–9.39 have each been synthesised from 7-Iodo-2-methyl-4-pyrrolidin-1-yl-quinoline and the respective boronic acid or the 4,4,5,5-tetramethyl-1,3,2-dioxaborolan-2-yl-derivative thereof comprised in the following starting material list.

| Ex. | Boronic acid or the 4,4,5,5-tetramethyl-1,3,2-dioxaborolan-2-yl-derivative thereof | Product Name | $MH^+$ found |
|---|---|---|---|
| 9.2 | 4-Ethylphenylboronic acid (commercially available) | 7-(4-Ethyl-phenyl)-2-methyl-4-pyrrolidin-1-yl-quinoline; compound with formic acid | 317.4 |
| 9.3 | 3,4-Dimethoxyphenylboronic acid (commercially available) | 7-(3,4-Dimethoxy-phenyl)-2-methyl-4-pyrrolidin-1-yl-quinoline; compound with formic acid | 349.4 |
| 9.4 | 2,6-Difluorophenylboronic acid (commercially available) | 7-(2,6-Difluoro-phenyl)-2-methyl-4-pyrrolidin-1-yl-quinoline; compound with formic acid | 325.4 |
| 9.5 | 2,4-Dimethoxyphenylboronic acid (commercially available) | 7-(2,4-Dimethoxy-phenyl)-2-methyl-4-pyrrolidin-1-yl-quinoline; compound with formic acid | 349.4 |
| 9.6 | 4-Trifluoromethylboronic acid (commercially available) | 2-Methyl-4-pyrrolidin-1-yl-7-(4-trifluoromethyl-phenyl)-quinoline; compound with formic acid | 357.4 |
| 9.7 | 4-(Methylthio)-phenylboronic acid (commercially available) | 2-Methyl-7-(4-methylsulfanyl-phenyl)-4-pyrrolidin-1-yl-quinoline; compound with formic acid | 335.5 |
| 9.8 | 2-Methoxyphenylboronic acid (commercially available) | 7-(2-Methoxy-phenyl)-2-methyl-4-pyrrolidin-1-yl-quinoline; compound with formic acid | 319.4 |
| 9.9 | 3-Ethoxyphenylboronic acid (commercially available) | 7-(3-Ethoxy-phenyl)-2-methyl-4-pyrrolidin-1-yl-quinoline; compound with formic acid | 333.4 |
| 9.10 | 3-Acetamidophenylboronic acid (commercially available) | N-[3-(2-Methyl-4-pyrrolidin-1-yl-quinolin-7-yl)-phenyl]-acetamide; compound with formic acid | 346.4 |
| 9.11 | 4-Trifluoromethoxyboronic acid (commercially available) | 2-Methyl-4-pyrrolidin-1-yl-7-(4-trifluoromethoxy-phenyl)-quinoline; compound with formic acid | 373.4 |
| 9.12 | (3,4-Methylenedioxyphenyl)boronic acid (commercially available) | 7-Benzo[1,3]dioxol-5-yl-2-methyl-4-pyrrolidin-1-yl-quinoline; compound with formic acid | 333.4 |
| 9.13 | Benzo[B]furan-2-boronic acid (commercially available) | 7-Benzofuran-2-yl-2-methyl-4-pyrrolidin-1- | 329.4 |

-continued

| Ex. | Boronic acid or the 4,4,5,5-tetramethyl-1,3,2-dioxaborolan-2-yl-derivative thereof | Product Name | MH+ found |
|---|---|---|---|
| | | yl-quinoline; compound with formic acid | |
| 9.14 | Benzo[B]thiophene-2-boronic acid (commercially available) | 7-Benzo[b]thiophen-2-yl-2-methyl-4-pyrrolidin-1-yl-quinoline; compound with formic acid | 345.5 |
| 9.15 | 3-Chloro-4-fluorophenylboronic acid (commercially available) | 7-(3-Chloro-4-fluoro-phenyl)-2-methyl-4-pyrrolidin-1-yl-quinoline; compound with formic acid | 341.8 |
| 9.16 | 5-Acetyl-thiopheneboronic acid (commercially available) | 1-[5-(2-Methyl-4-pyrrolidin-1-yl-quinolin-7-yl)-thiophen-2-yl]-ethanone; compound with formic acid | 337.5 |
| 9.17 | 3,4-Dichlorophenylboronic acid (commercially available) | 7-(3,4-Dichloro-phenyl)-2-methyl-4-pyrrolidin-1-yl-quinoline; compound with formic acid | 358.3 |
| 9.18 | 2-Fluorophenylboronic acid (commercially available) | 7-(2-Fluoro-phenyl)-2-methyl-4-pyrrolidin-1-yl-quinoline; compound with formic acid | 307.4 |
| 9.19 | 1-Naphtaleneboronic acid (commercially available) | 2-Methyl-7-naphthalen-1-yl-4-pyrrolidin-1-yl-quinoline; compound with formic acid | 339.5 |
| 9.20 | 2-Chlorophenylboronic acid (commercially available) | 7-(2-Chloro-phenyl)-2-methyl-4-pyrrolidin-1-yl-quinoline; compound with formic acid | 323.8 |
| 9.21 | 4-Vinylphenylboronic acid (commercially available) | 2-Methyl-4-pyrrolidin-1-yl-7-(4-vinyl-phenyl)-quinoline; compound with formic acid | 315.4 |
| 9.22 | 3,5-Bis(trifluoromethyl)phenylboronic acid (commercially available) | 7-(3,5-Bis-trifluoromethyl-phenyl)-2-methyl-4-pyrrolidin-1-yl-quinoline; compound with formic acid | 425.4 |
| 9.23 | 3-Methoxyphenylboronic acid (commercially available) | 7-(3-Methoxy-phenyl)-2-methyl-4-pyrrolidin-1-yl-quinoline; compound with formic acid | 319.4 |
| 9.24 | 3-(4,4,5,5-Tetramethyl-[1,3,2]dioxaborolan-2-yl)-benzoic acid ethyl ester (Lit.: WO 0027853A1) | 3-(2-Methyl-4-pyrrolidin-1-yl-quinolin-7-yl)-benzoic acid ethyl ester; compound with formic acid | 361.5 |
| 9.25 | 4-(4,4,5,5-Tetramethyl-[1,3,2]dioxaborolan-2-yl)-benzoic acid ethyl ester (commercially available) | 4-(2-Methyl-4-pyrrolidin-1-yl-quinolin-7-yl)-benzoic acid ethyl ester; compound with formic acid | 361.5 |
| 9.26 | 2-Methoxy-4-(4,4,5,5-tetramethyl-[1,3,2]dioxaborolan-2-yl)-phenol (Lit.: WO 0027853A1) | 2-Methoxy-4-(2-methyl-4-pyrrolidin-1-yl-quinolin-7-yl)-phenol; compound with formic acid | 335.4 |
| 9.27 | N-[4-(4,4,5,5-Tetramethyl-[1,3,2]dioxaborolan-2-yl)-phenyl]-acetamide (commercially available) | N-[4-(2-Methyl-4-pyrrolidin-1-yl quinolin-7-yl)-phenyl]-acetamide; compound | 346.4 |

-continued

| Ex. | Boronic acid or the 4,4,5,5-tetramethyl-1,3,2-dioxaborolan-2-yl-derivative thereof | Product Name | MH+ found |
|---|---|---|---|
| 9.28 | Dimethyl-[4-(4,4,5,5-tetramethyl-[1,3,2]dioxaborolan-2-yl)-phenyl]-amine (Lit.: J. Org. Chem. 2000, 65, 164–168) | Dimethyl-[4-(2-methyl-4-pyrrolidin-1-yl-quinolin-7-yl)-phenyl]-amine; compound with formic acid | 332.5 |
| 9.29 | 3,5-Dichlorophenylboronic acid (commercially available) | 7-(3,5-Dichloro-phenyl)-2-methyl-4-pyrrolidin-1-yl-quinoline; compound with formic acid | 358.3 |
| 9.30 | 2-Naphtaleneboronic acid (commercially available) | 2-Methyl-7-naphthalen-2-yl-4-pyrrolidin-1-yl-quinoline; compound with formic acid | 339.5 |
| 9.31 | N-Methyl-4-(4,4,5,5-tetramethyl-[1,3,2]dioxaborolan-2-yl)-benzamide (Lit.: WO 9845265A1) | N-Methyl-4-(2-methyl-4-pyrrolidin-1-yl-quinolin-7-yl)-benzamide; compound with formic acid | 346.4 |
| 9.32 | 3-(4,4,5,5-Tetramethyl-[1,3,2]dioxaborolan-2-yl)-phenol (commercially available) | 3-(2-Methyl-4-pyrrolidin-1-yl-quinolin-7-yl)-phenol; compound with formic acid | 305.4 |
| 9.33 | 2-Methoxy-5-(4,4,5,5-tetramethyl-[1,3,2]dioxaborolan-2-yl)-phenol (Lit.: WO 0027853A1) | 2-Methoxy-5-(2-methyl-4-pyrrolidin-1-yl-quinolin-7-yl)-phenol; compound with formic acid | 335.4 |
| 9.34 | 2,6-Dimethoxy-3-(4,4,5,5-tetramethyl-[1,3,2]dioxaborolan-2-yl)-pyridine (Lit.: WO 9845265A1) | 7-(2,6-Dimethoxy-pyridin-3-yl)-2-methyl-4-pyrrolidin-1-yl-quinoline; compound with formic acid | 350.4 |
| 9.35 | 2-(4,4,5,5-Tetramethyl-[1,3,2]dioxaborolan-2-yl)-phenol (Lit.: WO 0027853A1) | 2-(2-Methyl-4-pyrrolidin-1-yl-quinolin-7-yl)-phenol; compound with formic acid | 305.4 |
| 9.36 | 4,4,5,5-Tetramethyl-2-(4-phenoxy-phenyl)-[1,3,2]dioxaborolane (Lit.: WO 0027853A1) | 2-Methyl-7-(4-phenoxy-phenyl)-4-pyrrolidin-1-yl-quinoline; compound with formic acid | 381.5 |
| 9.37 | 2-(2,6-Dichloro-phenyl)-4,4,5,5-tetramethyl-[1,3,2]dioxaborolane (Lit.: J. Chromatogr. 1979, 186, 307–316) | 7-(2,6-Dichloro-phenyl)-2-methyl-4-pyrrolidin-1-yl-quinoline; compound with formic acid | 358.3 |
| 9.38 | 3-Trifluoromethoxyboronic acid (commercially available) | 2-Methyl-4-pyrrolidin-1-yl-7-(3-trifluoromethoxy-phenyl)-quinoline; compound with formic acid | 373.4 |
| 9.39 | 2-Trifluoromethoxyboronic acid (commercially available) | 2-Methyl-4-pyrrolidin-1-yl-7-(2-trifluoromethoxy-phenyl)-quinoline; compound with formic acid | 373.4 |

Example A

A compound of formula I can be used in a manner known per se as the active ingredient for the production of tablets of the following composition:

| | Per tablet |
|---|---|
| Active ingredient | 200 mg |
| Microcrystalline cellulose | 155 mg |

-continued

| Per tablet | |
|---|---|
| Corn starch | 25 mg |
| Talc | 25 mg |
| Hydroxypropylmethylcellulose | 20 mg |
| | 425 mg |

Example B

A compound of formula I can be used in a manner known per se as the active ingredient for the production of capsules of the following composition:

| Per capsule | |
|---|---|
| Active ingredient | 100.0 mg |
| Corn starch | 20.0 mg |
| Lactose | 95.0 mg |
| Talc | 4.5 mg |
| Magnesium stearate | 0.5 mg |
| | 220.0 mg |

Example C

Tablets containing the following ingredients can be manufactured in a conventional manner:

| Ingredients | Per tablet |
|---|---|
| Compound of formula I | 10.0–100.0 mg |
| Lactose | 125.0 mg |
| Maize starch | 75.0 mg |
| Talc | 4.0 mg |
| Magnesium stearate | 1.0 mg |

Example D

Capsules containing the following ingredients can be manufactured in a conventional manner:

| Ingredients | Per capsule |
|---|---|
| Compound of formula I | 25.0 mg |
| Lactose | 150.0 mg |
| Maize starch | 20.0 mg |
| Talc | 5.0 mg |

Example E

Injection solutions can have the following composition:

| Compound of formula I | 3.0 mg |
|---|---|
| Gelatine | 150.0 mg |
| Phenol | 4.7 mg |
| Water for injection solutions | ad 1.0 ml |

What is claimed is:

1. A compound selected from the group consisting of compounds of Formula I

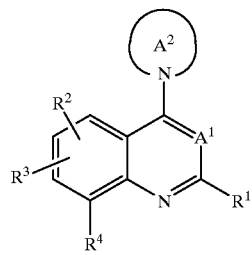

wherein
$R^1$ is alkyl, cycloalkyl, aralkyl or trifluoroalkyl;
$R^2$ is hydrogen, alkyl, alkoxy, hydroxy, halogen, trifluoroalkyl, difluoroalkoxy or trifluoroalkoxy;
$R^3$ is aryl or heteroaryl;
$R^4$ is hydrogen;
$R^5$ is hydrogen, alkyl or aralkyl;
$R^6$ and $R^7$ are each independently hydrogen or alkyl;
$A^1$ is CH;
$A^2$ is pryrolidine, piperidine, 3-4-dihydro-1H-isoquinoline, or azepane, each of which is optionally substituted with a group selected from the group consisting of alkyl, hydroxy, alkoxy, alkoxyalkyl, alkoxyalkoxy, hydroxyalkoxy, —$COOR^5$ and —$CONR^6R^7$;
pharmaceutically acceptable salts of compounds of Formula I, pharmaceutically acceptable solvates of compounds of Formula I and pharmaceutically acceptable esters of compounds of Formula I.

2. The compound according to claim 1, wherein $R^2$ is hydrogen.

3. The compound according to claim 1, wherein $R^1$ is alkyl.

4. The compound according to claim 3, wherein $R^1$ is methyl.

5. The compound according to claim 1, wherein $R^3$ is attached at the 7-position of the quinoline or quinazoline ring.

6. The compound according to claim 1, wherein $A^1$ is CH.

7. The compound according to claim 1, wherein $R^3$ is unsubstituted phenyl, thiophenyl, pyridinyl, pyrimidinyl, 1H-indolyl, benzofuryl, benzothiophenyl or naphthyl or $R^3$ is phenyl, thiophenyl, pyridinyl, pyrimidinyl, 1H-indolyl, benzofuryl, benzothiophenyl or naphthyl, substituted with one to three substituents each independently selected from halogen, trifluoromethyl, amino, alkoxy, methylendioxy, alkylcarbonyl, cyano, alkyl, nitro, hydroxy, trifluoromethoxy, alkylsulfanyl, alkenyl, alkoxycarbonyl, aryloxy, alkoxycarbonylamino, alkylcarbonylamino and aminocarbonyl.

8. The compound according to claim 7, wherein $R^3$ is unsubstituted thiophenyl, pyridinyl or naphthyl or $R^3$ is phenyl or thiophenyl substituted with one or two substituents each independently selected from halogen, trifluoromethyl, alkoxy, alkylcarbonyl, cyano and hydroxy.

9. The compound according to claim 7, wherein $A^2$ is pyrrolidine, piperidine, 3,4-dihydro 1H isoquinoline or azepane ring, wherein these rings are optionally substituted with alkyl.

10. The compound according to claim 9, selected from the group consisting of 4-(3,4-dihydro-1H-isoquinolin-2-yl)-2-methyl-7-(3-trifluoromethyl-phenyl)-quinoline, pharmaceutically acceptable salts thereof and pharmaceutically acceptable esters thereof.

11. The compound according to claim 10, which is 4-(3,4-dihydro-1H-isoquinolin-2-yl)-2-methyl-7-(3-trifluoromethyl-phenyl)-quinoline.

12. A compound selected from the group consisting of compounds of Formula Ia

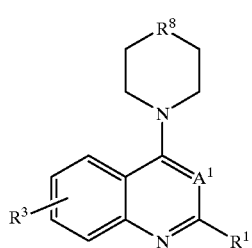

wherein
$R^1$ is lower alkyl;
$R^3$ is aryl or heteroaryl attached at the 5, 6 or 7-position of the quinoline or quinazoline ring;
$A^1$ is CH;
$R^8$ is a bond, or lower alkylene;
pharmaceutically acceptable salts of compounds of Formula Ia, and
pharmaceutically acceptable esters of compounds of Formula Ia.

13. The compound according to claim 12, wherein $R^3$ is unsubstituted phenyl, thiophenyl, pyridinyl, pyrimidinyl, 1H-indolyl, benzofuryl, benzothiophenyl or naphthyl or $R^3$ is phenyl, thiophenyl, pyridinyl, pyrimidinyl, 1H-indolyl, benzofuryl, benzothiophenyl or naphthyl, substituted with one to three substituents each independently selected from halogen, trifluoromethyl, amino, alkoxy, methylendioxy, alkylcarbonyl, cyano, alkyl, nitro, hydroxy, trifluoromethoxy, alkylsulfanyl, alkenyl, alkoxycarbonyl, aryloxy, alkoxycarbonylamino, alkylcarbonylamino and aminocarbonyl.

14. The compound according to claim 13, wherein $R^3$ is attached at the 7-position of the quinoline ring.

15. The compound according to claim 14, wherein $R^8$ is a bond.

16. The compound according to claim 15, wherein $R^3$ is an unsubstituted group selected from the group consisting of phenyl, thiophenyl, pyridinyl, pyrimidinyl, 1H-indolyl, benzofuryl, benzothiophenyl and naphthyl.

17. The compound according to claim 16, selected from the group consisting of 2-methyl-7-phenyl-4-pyrrolidin-1-yl-quinoline, pharmaceutically acceptable salts thereof and pharmaceutically acceptable esters thereof.

18. The compound according to claim 17, which is 2-methyl-7-phenyl-4-pyrrolidin-1-yl-quinoline.

19. The compound according to claim 16, selected from the group consisting of 2-methyl-4-pyrrolidin-1-yl-7-thiophen-2yl-quinoline, pharmaceutically acceptable salts thereof and pharmaceutically acceptable esters thereof.

20. The compound according to claim 19, which is 2-methyl-4-pyrrolidin-1-yl-7-thiophen-2yl-quinoline.

21. The compound according to claim 16, selected from the group consisting of 2-methyl-7-pyridin-3-yl-4-pyrrolidin-1-yl-quinoline, pharmaceutically acceptable salts thereof and pharmaceutically acceptable esters thereof.

22. The compound according to claim 21, which is 2-methyl-7-pyridin-3-yl-4-pyrrolidin-1-yl-quinoline.

23. The compound according to claim 16, selected from the group consisting of 2-methyl-7-pyrimidin-5-yl-4-pyrrolidin-1-yl-quinoline, pharmaceutically acceptable salts thereof and pharmaceutically acceptable esters thereof.

24. The compound according to claim 23, which is 2-methyl-7-pyrimidin-5-yl-4-pyrrolidin-1-yl-quinoline.

25. The compound according to claim 15, wherein $R^3$ is selected from the group consisting of phenyl, thiophenyl, pyridinyl, pyrimidinyl, 1H-indolyl, benzofuryl, benzothiophenyl and naphthyl, and is substituted with one to three substituents; wherein each substituent is selected from the group consisting of halogen, trifluoromethyl, amino, alkoxy, methylendioxy, alkylcarbonyl, cyano, alkyl, nitro, hydroxy, trifluoromethoxy, alkylsulfanyl, alkenyl, alkoxycarbonyl, aryloxy, alkoxycarbonylamino, alkylcarbonylamino and aminocarbonyl.

26. The compound according to claim 25, selected from the group consisting of 7-(3-chloro-phenyl)-2-methyl-4-pyrrolidin-1-yl-quinoline, pharmaceutically acceptable salts thereof and pharmaceutically acceptable esters thereof.

27. The compound according to claim 26, which is 7-(3-chloro-phenyl)-2-methyl-4-pyrrolidin-1-yl-quinoline.

28. The compound according to claim 25, selected from the group consisting of 2-methyl-4-pyrrolidin-1-yl-7-(3-trifluoromethyl-phenyl)-quinoline, pharmaceutically acceptable salts thereof and pharmaceutically acceptable esters thereof.

29. The compound according to claim 28, which is 2-methyl-4-pyrrolidin-1-yl-7-(3-trifluoromethyl-phenyl)-quinoline.

30. The compound according to claim 25, selected from the group consisting of 3-(2-methyl-4-pyrrolidin-1-yl-quinoline-7-yl)-phenylamine, pharmaceutically acceptable salts thereof and pharmaceutically acceptable esters thereof.

31. The compound according to claim 30, which is 3-(2-methyl-4-pyrrolidin-1-yl-quinoline-7-yl)-phenylamine.

32. The compound according to claim 25, selected from the group consisting of 1-[4-(2-methyl-4-pyrrolidin-1-yl-quinoline-7-yl)-phenyl]-ethanone, pharmaceutically acceptable salts thereof and pharmaceutically acceptable esters thereof.

33. The compound according to claim 32, which is 1-[4-(2-methyl-4-pyrrolidin-1-yl-quinoline-7-yl)-phenyl]-ethanone.

34. The compound according to claim 25, selected from the group consisting of 7-(4-methoxy-phenyl)-2-methyl-4-pyrrolidin-1-yl-quinoline, pharmaceutically acceptable salts thereof and pharmaceutically acceptable esters thereof.

35. The compound according to claim 34, which is 7-(4-methoxy-phenyl)-2-methyl-4-pyrrolidin-1-yl-quinoline.

36. The compound according to claim 14, wherein $R^8$ is lower alkylene.

37. The compound according to claim 36, wherein $R^8$ is a methylene group.

38. The compound according to claim 37, wherein $R^3$ is an unsubstituted group selected from the group consisting of phenyl, thiophenyl, pyridinyl, pyrimidinyl, 1H-indolyl, benzofuryl, benzothiophenyl and naphthyl.

39. The compound according to claim 38, selected from the group consisting of 2-methyl-4-piperidin-1-yl-7-thiophen-2-yl-quinoline, pharmaceutically acceptable salts thereof and pharmaceutically acceptable esters thereof.

40. The compound according to claim 39, which is 2-methyl-4-piperidin-1-yl-7-thiophen-2-yl-quinoline.

41. The compound according to claim 38, selected from the group consisting of 2-methyl-7-phenyl-4-piperidin-1-yl-quinoline, pharmaceutically acceptable salts thereof and pharmaceutically acceptable esters thereof.

42. The compound according to claim 41, which is 2-methyl-7-phenyl-4-piperidin-1-yl-quinoline.

43. The compound according to claim 38, selected from the group consisting of 7-(1H-indol-5-yl)-2-methyl-4-piperidin-1-yl-quinoline, pharmaceutically acceptable salts thereof and pharmaceutically acceptable esters thereof.

44. The compound according to claim 43, which is 7-(1H-indol-5-yl)-2-methyl-4-piperidin-1-yl-quinoline.

45. The compound according to claim 38, selected from the group consisting of 2-methyl-4-piperidin-1-yl-7-pyridin-3-yl-quinoline, pharmaceutically acceptable salts thereof and pharmaceutically acceptable esters thereof.

46. The compound according to claim 45, which is 2-methyl-4-piperidin-1-yl-7-pyridin-3-yl-quinoline.

47. The compound according to claim 37, wherein $R^3$ is selected from the group consisting of phenyl, thiophenyl, pyridinyl, pyrimidinyl, 1H-indolyl, benzofuryl, benzothiophenyl and naphthyl, and is substituted with one to three substituents; wherein each substituent is selected from the group consisting of halogen, trifluoromethyl, amino, alkoxy, methylendioxy, alkylcarbonyl, cyano, alkyl, nitro, hydroxy, trifluoromethoxy, alkylsulfanyl, alkenyl, alkoxycarbonyl, aryloxy, alkoxycarbonylamino, alkylcarbonylamino and aminocarbonyl.

48. The compound according to claim 47, selected from the group consisting of 2-methyl-4-piperidin-1-yl-7-(3-trifluoromethyl-phenyl)-quinoline pharmaceutically acceptable salts thereof and pharmaceutically acceptable esters thereof.

49. The compound according to claim 48, which is 2-methyl-4-piperidin-1-yl-7-(3-trifluoromethyl-phenyl)-quinoline.

50. The compound according to claim 47, selected from the group consisting of 7-(3-choro-phenyl)-2-methyl-4-piperidin-1-yl-quinoline, pharmaceutically acceptable salts thereof and pharmaceutically acceptable esters thereof.

51. The compound according to claim 50, which is 7-(3-choro-phenyl)-2-methyl-4-piperidin-1-yl-quinoline.

52. The compound according to claim 47, selected from the group consisting of 1-[4-(2-methyl-4-piperidin-1-yl-quinolin-7-yl)-phenyl]-ethanone, pharmaceutically acceptable salts thereof and pharmaceutically acceptable esters thereof.

53. The compound according to claim 52, which is 1-[4-(2-methyl-4-piperidin-1-yl-quinolin-7-yl)-phenyl]-ethanone.

54. The compound according to claim 47, selected from the group consisting of 3-(2-methyl-4-piperidin-1-yl-quinolin-7-yl)-phenylamine, pharmaceutically acceptable salts thereof and pharmaceutically acceptable esters thereof.

55. The compound according to claim 54, which is 3-(2-methyl-4-piperidin-1-yl-quinolin-7-yl)-phenylamine.

56. The compound according to claim 47, selected from the group consisting of 7-(4-methoxy-phenyl)-2-methyl-4-piperidin-1-yl-quinoline, pharmaceutically acceptable salts thereof and pharmaceutically acceptable esters thereof.

57. The compound according to claim 56, which is 7-(4-methoxy-phenyl)-2-methyl-4-piperidin-1-yl-quinoline.

58. The compound according to claim 36, wherein $R^8$ is an ethylene group.

59. The compound according to claim 58, wherein $R^3$ is an unsubstituted group selected from the group consisting of phenyl, thiophenyl, pyridinyl, pyrimidinyl, 1H-indolyl, benzofuryl, benzothiophenyl and naphthyl.

60. The compound according to claim 58, wherein $R^3$ is selected from the group consisting of phenyl, thiophenyl, pyridinyl, pyrimidinyl, 1H-indolyl, benzofuryl, benzothiophenyl and naphthyl, and is substituted with one to three substituents; wherein each substituent is selected from the group consisting of halogen, trifluoromethyl, amino, alkoxy, methylendioxy, alkylcarbonyl, cyano, alkyl, nitro, hydroxy, trifluoromethoxy, alkylsulfanyl, alkenyl, alkoxycarbonyl, aryloxy, alkoxycarbonylamino, alkylcarbonylamino and aminocarbonyl.

61. The compound according to claim 60, selected from the group consisting of 4-azepan-1-yl-2-methyl-7-(3-trifluoromethyl-phenyl)-quinoline, pharmaceutically acceptable salts thereof and pharmaceutically acceptable esters thereof.

62. The compound according to claim 61, which is 4-azepan-1-yl-2-methyl-7-(3-trifluoromethyl-phenyl)-quinoline.

63. The compound according to claim 13, wherein $R^3$ is attached at the 6-position of the quinoline ring.

64. The compound according to claim 63, wherein $R^8$ is a bond.

65. The compound according to claim 64, selected from the group consisting of 6-(3-chloro-phenyl)-2-methyl-4-pyrrolidin-1-yl-quinoline, pharmaceutically acceptable salts thereof and pharmaceutically acceptable esters thereof.

66. The compound according to claim 65, which is 6-(3-chloro-phenyl)-2-methyl-4-pyrrolidin-1-yl-quinoline.

67. The compound according to claim 63, wherein $R^8$ is lower alkylene.

68. The compound according to claim 13, wherein $R^3$ is attached at the 5-position of the quinoline ring.

69. The compound according to claim 68, wherein $R^8$ is a bond.

70. The compound according to claim 69, selected from the group consisting of 5-(3-chloro-phenyl)-2-methyl-4-pyrrolidin-1-yl-quinoline, pharmaceutically acceptable salts thereof and pharmaceutically acceptable esters thereof.

71. The compound according to claim 70, which is 5-(3-chloro-phenyl)-2-methyl-4-pyrrolidin-1-yl-quinoline.

72. The compound according to claim 68, wherein $R^8$ is lower alkylene.

73. The compound according to claim 72, selected from the group consisting of 5-(3-chloro-phenyl)-2-methyl-4-piperidin-1-yl-quinoline, pharmaceutically acceptable salts thereof and pharmaceutically acceptable esters thereof.

74. The compound according to claim 73, which is 5-(3-chloro-phenyl)-2-methyl-4-piperidin-1-yl-quinoline.

75. The compound according to claim 72, selected from the group consisting of 2-methyl-4-piperidin-1-yl-5-(3-trifluoromethyl-phenyl)-quinoline, pharmaceutically acceptable salts thereof and pharmaceutically acceptable esters thereof.

76. The compound according to claim 75, which is 2-methyl-4-piperidin-1-yl-5(3-trifluoromethyl-phenyl)-quinoline.

* * * * *

UNITED STATES PATENT AND TRADEMARK OFFICE
CERTIFICATE OF CORRECTION

PATENT NO. : 6,900,226 B2
DATED : May 31, 2005
INVENTOR(S) : Breu et al.

It is certified that error appears in the above-identified patent and that said Letters Patent is hereby corrected as shown below:

Title page,
Item [73], Assignee, "Hoffman-La Roche Inc." should be -- Hoffmann-La Roche Inc. --.

Signed and Sealed this

Thirtieth Day of August, 2005

JON W. DUDAS
*Director of the United States Patent and Trademark Office*